United States Patent [19]

Chapman et al.

[11] Patent Number: 5,434,248
[45] Date of Patent: Jul. 18, 1995

[54] PEPTIDYL DERIVATIVES AS INHIBITORS OF INTERLEUKIN-1β CONVERTING ENZYME

[75] Inventors: Kevin T. Chapman, Scotch Plains; Herb G. Bull, Westfield; Malcolm MacCoss, Freehold; Nancy A. Thornberry, Westfield; Jeffrey R. Weidner, Iselin; Adnan M. Mjalli, Rahway, all of

[73] Assignee: Merck & Co., Inc., Rahway, N.J.

[21] Appl. No.: 70,483

[22] Filed: Jun. 2, 1993

Related U.S. Application Data

[63] Continuation of Ser. No. 889,555, May 27, 1992, abandoned, which is a continuation-in-part of Ser. No. 811,157, Dec. 19, 1991, abandoned, which is a continuation-in-part of Ser. No. 718,892, Jun. 21, 1991, abandoned.

[51] Int. Cl.$^6$ .................. A61K 38/00; C07K 5/00; C07K 7/00; C07K 17/00
[52] U.S. Cl. ............................ 530/330; 530/331; 562/571
[58] Field of Search ............... 514/18, 19; 530/330, 530/331; 562/571

[56] References Cited

U.S. PATENT DOCUMENTS

| | | | |
|---|---|---|---|
| 4,582,821 | 4/1986 | Kettner et al. | 514/12 |
| 5,055,451 | 10/1991 | Krantz et al. | 514/19 |
| 5,278,061 | 1/1994 | Bull et al. | 435/212 |

FOREIGN PATENT DOCUMENTS

| | | |
|---|---|---|
| 0263202 | 4/1988 | European Pat. Off. . |
| WO91/15577 | 2/1991 | WIPO . |
| WO93/09135 | 5/1993 | WIPO . |

OTHER PUBLICATIONS

Sleath et al. J. Biol. Chem. vol. 265 No. 24 Aug. 1990, 14526–14528.
Patent Abstracts of Japan vol. 13, No. 227 (C-600) (3575) 25 May 1989 Appl. #62-194134.
Nature vol. 356, 30 Apr. 1992, London, England pp. 768–774 Thornberry, et al.
Black, et al. J. Biol. Chem. 263, 9437–9442 (1988).
Black, et al J. Biol. Chem. 264, 5323–5326 (1989).
Black, et al FEB LETT. 247, 286–290 (1989).
Kostura, et al Proc. Natl. Acad. Sci. 86, 5227–5231 (1989).
Sleath, et al J. Biol. Chem. 265, 14526–14528 (1990).
U.S. Ser. No. 746,942, filed Aug. 16, 1991 to Kostura et al, Docket No. 17934IA.
U.S. Ser. No. 746,454, filed Aug. 16, 1991, to Howard et al, Docket No. 18498.
U.S. Ser. No. 746,455, filed Aug. 16, 1991, to Chapman et al, Docket No. 18517.
U.S. Ser. No. 808,994, filed Dec. 17, 1991 to Chapman et al, Docket No. 18517IA.
U.S. Ser. No. 808,996, filed Dec. 17, 1991, to Chapman et al, Docket No. 18516IA.
U.S. Ser. No. 811,157, filed Dec. 19, 1991, to Chapman et al, Docket No. 18440IA.
U.S. Ser. No. 811,160, filed Dec. 19, 1991, to Chapman et al, Docket No. 18639.
U.S. Ser. No. 830,162, filed Jan. 31, 1992, to Chapman et al, Docket No. 18659.
U.S. Ser. No. 839,590, filed Feb. 21, 1992, to Chapman et al, Docket No. 18673.

Primary Examiner—Jill Warden
Assistant Examiner—Shella J. Huff
Attorney, Agent, or Firm—Curtis C. Panzer; David L. Rose

[57] ABSTRACT

Novel peptidyl derivatives of formula I are found to be potent inhibitors of interleukin-1β converting enzyme (ICE). Compounds of formula I may be useful in the treatment of inflammatory or immune-based diseases of the lung and airways; central nervous system and surrounding membranes; the eyes and ears; joints, bones, and connective tissues; cardiovascular system including the pericardium; the gastrointestinal and urogenital systems; the skin and mucosal membranes. Compounds of formula I are also useful in treating the complications of infection (e.g., gram negative shock) and tumors in which IL 1 functions as an autocrine growth factor or as a mediator of cachexia.

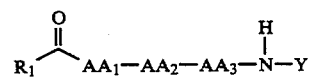

22 Claims, No Drawings

PEPTIDYL DERIVATIVES AS INHIBITORS OF INTERLEUKIN-1β CONVERTING ENZYME

This is a continuation of application Ser. No. 07/889,555, filed on May 27, 1992, now abandoned, which is a continuation-in-part of Ser. No. 07/811,157, filed Dec. 19, 1991, now abandoned, which is a continuation-in-part of Ser. No. 07/718,892, filed Jun. 21, 1991, now abandoned.

BACKGROUND OF THE INVENTION

This invention relates to substituted peptidyl derivatives useful in the treatment of inflammation in lung, central nervous system, kidney, joints, endocardium, pericardium, eyes, ears, skin, gastrointestinal tract and urogenital system. More particularly, this invention relates substituted peptidyl lactones and open forms thereof that are useful inhibitors of interleukin-1β converting enzyme (ICE). Interleukin-1β converting enzyme (ICE) has been identified as the enzyme responsible for converting precursor interleukin-1β (IL-1β) to biologically active IL-1β.

Mammalian interleukin-1 (IL-1) is an immunoregulatory protein secreted by cell types as part of the inflammatory response. The primary-cell type responsible for IL-1 production is the peripheral blood monocyte. Other cell types have also been described as releasing or containing IL-1 or IL-1 like molecules. These include epithelial cells (Luger, et al., J. Immunol. 127:1493–1498 (1981), Le et al., J. Immunol. 138:2520–2526 (1987) and Lovett and Larsen, J. Clin. Invest. 82:115–122 (1988), connective tissue cells (Ollivierre et al., Biochem. Biophys. Res. Comm. 141: 904–911 (1986), Le et al, J. Immunol. 138:2520–2526 (1987), cells of neuronal origin (Giulian et al., J. Esp. Med. 164: 594–604 (1986) and leukocytes (Pistoia et al., J. Immunol. 136: 1688–1692 (1986), Acres et al., Mol. Immuno. 24: 479–485 (1987), Acres et al., J. Immunol. 138: 2132–2136 (1987) and Lindenmann et al., J. Immunol 140: 837–839 (1988).

Biologically active IL-1 exists in two distinct forms, IL-1α with an isoelectric point of about pI 5.2 and IL-1β with an isoelectric point of about 7.0 with both forms having a molecular mass of about 17,500 (Bayne et al., J. Esp. Med. 163: 1267–1280 (1986) and Schmidt, J. Esp. Med. 160: 772 (1984). The polypeptides appear evolutionarily conserved, showing about 27–33% homology at the amino acid level (Clark et al., Nucleic Acids Res. 14: 7897–7914 (1986).

Mammalian IL-1β is synthesized as a cell associated precursor polypeptide with a molecular mass of about 31.4 kDa (Limjuco et al., Proc. Natl. Acad. Sci USA 83: 3972–3976 (1986). Precursor IL-1β is unable to bind to IL-1 receptors and is biologically inactive (Mosley et al., J. Biol. Chem. 262: 2941–2944 (1987). Biological activity appears dependent upon some form of proteolytic processing which results in the conversion of the precursor 31.5 kDa form to the mature 17.5 kDa form. Evidence is growing that by inhibiting the conversion of precursor IL-1β to mature IL-1β, one can effectively inhibit the activity of interleukin-1.

Mammalian cells capable of producing IL-1β include, but are not limited to, karatinocytes, endothelial cells, mesangial cells, thymic epithelial cells, dermal fibroblasts, chondrocytes, astrocytes, glioma cells, mononuclear phagocytes, granulocytes, T and B lymphocytes and NK cells.

As discussed by J. J. Oppenheim, et al. Immunology Today, vol. 7(2):45–56 (1986), the activities of interleukin-1 are many. It has been observed that catabolin, a factor that promotes degradation of cartilage matrix, also exhibited the thymocyte comitogenic activities of IL-1 and stimulates chondrocytes to release collagenase neutral proteases and plasminogen activator. In addition, a plasma factor termed proteolysis inducing factor stimulates muscle cells to produce prostaglandins which in turn leads to proteolysis, the release of amino acids and, in the long run, muscle wasting, and appears to represent a fragment of IL-1 with fever-inducing, acute phase response and thymocyte co-mitogenic activities.

IL-1 has multiple effects on cells involved in inflammation and wound healing. Subcutaneous injection of IL-1 leads to margination of neutrophils and maximal extravascular infiltration of the polymorphonuclear leukocytes (PMN). In vitro studies reveal IL-1 to be a chemotactic attractant for PMN to activate PMN to metabolize glucose more rapidly to reduce nitroblue tetrazolium and to release their lysozomal enzymes. Endothelial cells are stimulated to proliferate by IL-1 to produce thromboxane, to become more adhesive and to release procoagulant activity. IL-1 also enhances collagen type IV production by epidermal cells, induces osteoblast proliferation and alkaline phosphatase production and stimulates osteoclasts to resorb bone. Even macrophages have been reported to be chemotactically attracted to IL-1 to produce prostaglandins in response to IL-1 and to exhibit a more prolonged and active tumoricidal state.

IL-1 is also a potent bone resorptive agent capable upon infusion into mice of causing hypercaleemia and increase in bone resorptive surface as revealed by his to morphometry Sabatini, M. et al., PNAS 85: 5235–5239, 1988.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix. Such diseases include periodonate diseases interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

SUMMARY OF THE INVENTION

Novel peptidyl aldehydes, ring chain tautomers and hydrates thereof of formula I are found to be potent inhibitors of interleukin-1β converting enzyme (ICE).

Compounds of formula I are useful in the treatment of deseases including inflammation in lung, central nervous system, kidney, joints, endocardium, pericardium, eyes, ears, skin, gastrointestinal tract and urogenital system.

DETAILED DESCRIPTION OF THE INVENTION

The invention encompasses compounds of formula I.

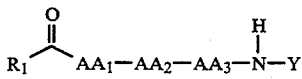

or a pharmaceutically acceptable salt thereof thereof: wherein Y is:

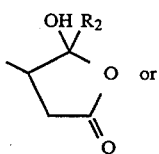

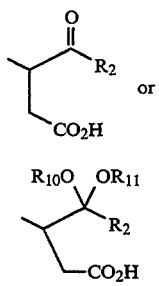

$R_1$ is
- (a) substituted $C_{1-12}$ alkyl, wherein the substituent is selected from
  - (1) hydrogen,
  - (2) hydroxy,
  - (3) halo, and
  - (4) $C_{1-6}$ alkylcarbonyl;
- (b) aryl $C_{1-6}$ alkyl wherein the aryl group is selected from the group consisting of:
  - (1) phenyl,
  - (2) naphthyl,
  - (3) pyridyl,
  - (4) furyl,
  - (5) thienyl,
  - (6) thiazolyl,
  - (7) isothiazolyl,
  - (8) imidazolyl,
  - (9) benzimidazolyl,
  - (10) pyrazinyl,
  - (11) pyrimidyl,
  - (12) quinolyl,
  - (13) isoquinolyl,
  - (14) benzofuryl,
  - (15) benzothienyl,
  - (16) pyrazolyl,
  - (17) indolyl,
  - (18) purinyl,
  - (19) isoxazolyl, and
  - (20) oxazolyl, and mono and di-substituted aryl as defined above in items (1) to (20) wherein the substitutents are independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

$R_2$ is
- (a) H,
- (b) deuterium,

wherein $R_3$ is
  - (1) substituted $C_{1-6}$ alkyl, wherein the substituent is selected from
    - (a) hydrogen,
    - (b) hydroxy,
    - (c) halo, and
    - (d) $C_{1-6}$ alkyl carbonyl,
  - (2) aryl $C_{1-6}$ alkyl or substituted aryl $C_{1-6}$ alkyl as defined as defined above, wherein the aryl may be mono and di-substituted the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

wherein $R_4$ and $R_5$ are each individually selected from hydrogen, fluorine and hydroxy;

$R_6$ is selected from the group consisting of
  - (1) hydrogen,
  - (2) fluorine,
  - (3) substituted $C_{1-6}$ alkyl wherein the substituent is selected from
    - (a) hydrogen,
    - (b) hydroxy,
    - (c) halo,
    - (d) $C_{1-6}$ alkylcarbonyl,
  - (4) aryl $C_{1-6}$ alkyl, wherein the alkyl is substituted with hydrogen, oxo, $C_{1-3}$ alkyl, halo or hydroxy, wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

- (5) $C_{1-6}$ alkyl amino carbonyl $C_{1-6}$ alkyl or $C_{1-6}$ alkyl carbonyl amino $C_{1-6}$ alkyl,
  - (6) aryl amino carbonyl $C_{1-6}$ alkyl or aryl carbonyl amino $C_{1-6}$ alkyl, wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

- (7) aryl $C_{1-6}$ alkyl amino carbonyl $C_{1-6}$ alkyl or aryl $C_{1-6}$ alkyl carbonyl amino $C_{1-6}$ alkyl, wherein aryl is defined as immediately above, and wherein the aryl may be mono and di-substituted, the substituents being each independently $C_{1-6}$ alkyl, halo, hydroxy, $C_{1-6}$ alkyl amino, $C_{1-6}$ alkoxy, $C_{1-6}$ alkylthio, and $C_{1-6}$ alkylcarbonyl;

$R_{10}$ and $R_{11}$ are each independently (a) hydrogen,
(b) $C_{1-6}$ alkyl,
(c) aryl $C_{1-6}$ alkyl, wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl, and
(20) oxazolyl,
and mono and di-substituted aryl as defined above in items (1) to (20) wherein the substituents are independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl, or $R_{10}$ and $R_{11}$ are joined together to form a ring of 5 to 7 carbon atoms, said ring having 2 heteroatoms;
$AA_1$ is independently selected from the group consisting of
(a) a single bond, and
(b) an amino acid of formula AI

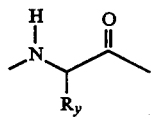

wherein $R_7$ is selected from the group consisting of:
(a) hydrogen,
(b) substituted $C_{1-6}$ alkyl, wherein the substituent is selected from
(1) hydrogen,
(2) hydroxy,
(3) halo,
(4) —S-$C_{1-4}$ alkyl
(5) —SH
(6) $C_{1-6}$ alkylcarbonyl,
(7) carboxy, O
(8) —$CNH_2$,
(9) amino carbonyl amino,
(10) $C_{1-4}$ alkylamino, wherein the alkyl moiety is substituted with hydrogen or hydroxy, and the amino is substituted with hydrogen or CBZ,
(11) guanidino, and
(c) aryl $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.
$AA_2$ is independently selected from the group consisting of
(a) a single bond, and
(b) an amino acid of formula AII

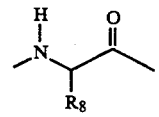

$AA_3$, which are each independently selected from the group consisting of
(a) a single bond, and
(b) an amino acid of formula AIII

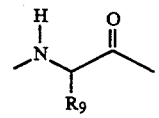

wherein $R_8$ and $R_9$ are each independently selected from the group consisting of
(a) hydrogen,
(b) substituted $C_{1-6}$ alkyl, wherein the substituent is selected from
(1) hydrogen,
(2) hydroxy,
(3) halo,
(4) —S-$C_{1-4}$ alkyl
(5) —SH
(6) $C_{1-6}$ alkylcarbonyl,
(7) carboxy,

(9) amino carbonyl amino,
(10) $C_{1-4}$ alkylamino, wherein the alkyl moiety is substituted with hydrogen or hydroxy, and the amino is substituted with hydrogen or CBZ,
(11) guanidino, and
(c) aryl $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.
One class of this genus is the compounds wherein:
$R_1$ is
(a) substituted $C_{1-6}$ alkyl, wherein the substituent is selected from
(1) hydrogen,
(2) hydroxy,
(3) chloro or fluoro, and
(b) aryl $C_{1-6}$ alkyl wherein the aryl group is selected from the group consisting of
(1) phenyl,
(2) naphthyl,
(3) pyridyl,
(4) furyl,
(5) thienyl,
(6) thiazolyl,
(7) isothiazolyl,
(8) benzofuryl,
(9) benzothienyl,
(10) indolyl,
(11) isooxazolyl, and
(12) oxazolyl, and mono and di-substituted $C_{6-10}$aryl as defined above in items (1) to (12) wherein the substituents are independently $C_{1-4}$alkyl, halo, and hydroxy;

$R_2$ is
(a) H,
(b) deuterium,

 (c)

wherein $R_4$ and $R_5$ are each individually selected from hydrogen, fluorine and hydroxy;

$R_6$ is selected from the group consisting of
(1) hydrogen,
(2) fluorine,
(3) substituted $C_{1-6}$ alkyl wherein the substituent is selected from
(a) hydrogen,
(b) hydroxy,
(c) halo,
(d) $C_{1-6}$ alkylcarbonyl,
(4) aryl $C_{1-6}$ alkyl,
wherein the alkyl is substituted with hydrogen, oxo, $C_{1-3}$ alkyl, halo or hydroxy, wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;
(5) $C_{1-6}$ alkyl amino carbonyl $C_{1-6}$ alkyl or $C_{1-6}$ alkyl carbonyl amino $C_{1-6}$ alkyl,
(6) aryl amino carbonyl $C_{1-6}$ alkyl or aryl carbonyl amino C1-6 alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;
(7) aryl $C_{1-6}$ alkyl amino carbonyl $C_{1-6}$ alkyl or aryl $C_{1-6}$ alkyl carbonyl amino $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$R_{10}$ and $R_{11}$ are each independently hydrogen or $C_{1-3}$ alkyl;

$AA_1$ is independently selected from the group consisting of
(a) a single bond, and
(b) an amino acid of formula AI

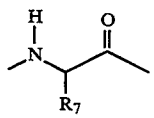

wherein $R_7$ is aryl $C_{1-6}$ alkyl wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl;

$AA_2$ is independently selected from the group consisting of
(a) a single bond, and
(b) an amino acid of formula AII

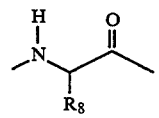

$AA_3$, which are each independently selected from the group consisting of
(a) a single bond, and
(b) an amino acid of formula AIII

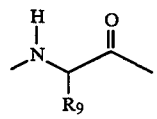

wherein $R_8$ and $R_9$ are each independently selected from the group consisting of
(a) hydrogen,
(b) $C_{1-6}$ alkyl, wherein the substituent is selected from
(1) hydrogen,
(2) hydroxy,
(3) halo,
(4) —S—$C_{1-4}$ alkyl
(5) —SH
(6) $C_{1-6}$ alkylcarbonyl,
(7) carboxy,

 (8)

(9) $C_{1-4}$ alkylamino, and $C_{1-4}$ alkyl amino wherein the alkyl moiety is substituted with an hydroxy, and
(10) guanidino, and
(c) aryl $C_{1-6}$ alkyl,
wherein aryl is defined as immediately above, and wherein the aryl may be mono and di-substituted, the substituents being each independently $C_{1-6}$alkyl, halo, hydroxy, $C_{1-6}$alkyl amino, $C_{1-6}$alkoxy, $C_{1-6}$alkylthio, and $C_{1-6}$alkylcarbonyl.

Within this class are the compounds wherein AA1, AA2 and AA3, are each independently selected from the group consisting of the L- and D- forms of the amino acids including glycine, alanine, valine, leucine, isoleucine, setins, threonine, aspartic acid, asparagine, glutamic acid, glutamine, lysine, hydroxy-lysine, histidine, arginine, phenylalanine, tyrosine, tryptophan, cysteine, methionine, ornithine, β-alanine, homoserine, homotyrosine, homophenylalanine and citrulline.

Alternatively, within this class are the subclass of compounds wherein
$R_1$ is $C_{1-3}$alkyl;
$R_2$ is hydrogen, deuterium or

and
$R_8$ and $R_9$ are each individually
(a) hydrogen,
(b) $C_{1-6}$alkyl,
(c) mercapto $C_{1-6}$alkyl,
(d) hydroxy $C_{1-6}$alkyl, (e) carboxy $C_{1-6}$alkyl,
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) amino-$C_{1-6}$alkyl or N-substituted amino-$C_{1-6}$alkyl wherein the substituent is carbobenzoxy,
(k) carbamyl $C_{1-6}$alkyl, or
(l) aryl $C_{1-6}$alkyl, wherein the aryl group is selected from phenyl and indolyl, and the aryl group may be substituted with hydroxy, $C_{1-3}$ alkyl.

Within this sub-class are the compounds wherein:
$R_1$ is methyl;
$R_2$ is hydrogen;
$R_8$ is $C_{1-6}$alkyl; and
$R_9$ is
(a) hydrogen,
(b) $C_{1-6}$alkyl,
(d) benzyl,
(e) p-hydroxy-benzyl,
(f) N-carbobenzoxy-amino-(n-butyl),
(g) carbamylmethyl,
(h) carbamylethyl,
(i) indol-2-yl-methyl,
(j) substituted phenyl $C_{1-6}$alkyl, wherein the substituent is hydrogen, hydroxy, carboxy, or $C_{1-4}$alkyl,
(k) substituted indolyl $C_{1-6}$alkyl, wherein the substituent is hydrogen, hydroxy, carboxy, or $C_{1-4}$alkyl, or
(l) substituted imidazolyl $C_{1-6}$alkyl wherein the substituent is hydrogen, hydroxy, carboxy, or $C_{1-4}$alkyl.

Exemplifying the invention are the following compounds:
(a) N-(N-Acetyl-tyrosinyl-valinyl-lysinyl)-3-amino-4-oxobutanoic acid;
(b) N-(N-Acetyl-tyrosinyl-valinyl-ε-CBZ-lysinyl)-3-amino-4-oxobutanoic acid;
(c) N-(N-Acetyl-tyrosinyl-valinyl-lysinyl)-3-amino-4-oxobutanoic acid; or a ring chain tautomer or hydrate thereof.

For purposes of this specification the above description for the compounds which explicitly correspond to the following equilibrium form of Y

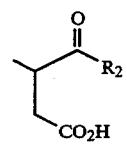

are intended to include the following equilibrium forms as well:

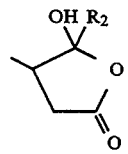

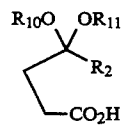

This invention also concerns to pharmaceutical composition and methods of treatment of interleukin-1 and interleukin-1β mediated or implicated disorders or diseases (as described above) in a patient (including man and/or mammalian animals raised in the dairy, meat, or fur industries or as pets) in need of such treatment comprising administration of interleukin-1β inhibitors of formula (I) as the active constituents.

Illustrative of these aspects, this invention concerns pharmaceutical compositions and methods of treatment of diseases selected from septic shock, allograft rejection, inflammatory bowel disease and rheumatoid arthritis in a patient in need of such treatment comprising:
administration of an interleukin-1β inhibitor of formula (I) as the active constituent.

Compounds of the instant invention are conveniently prepared using the procedures described generally below and more explicitly described in the Example section thereafter.

Scheme I

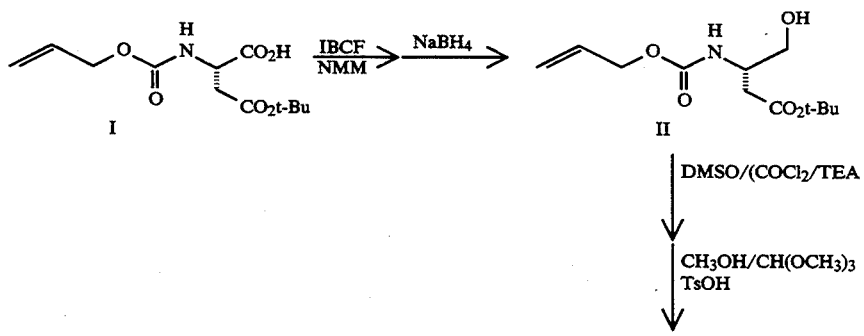

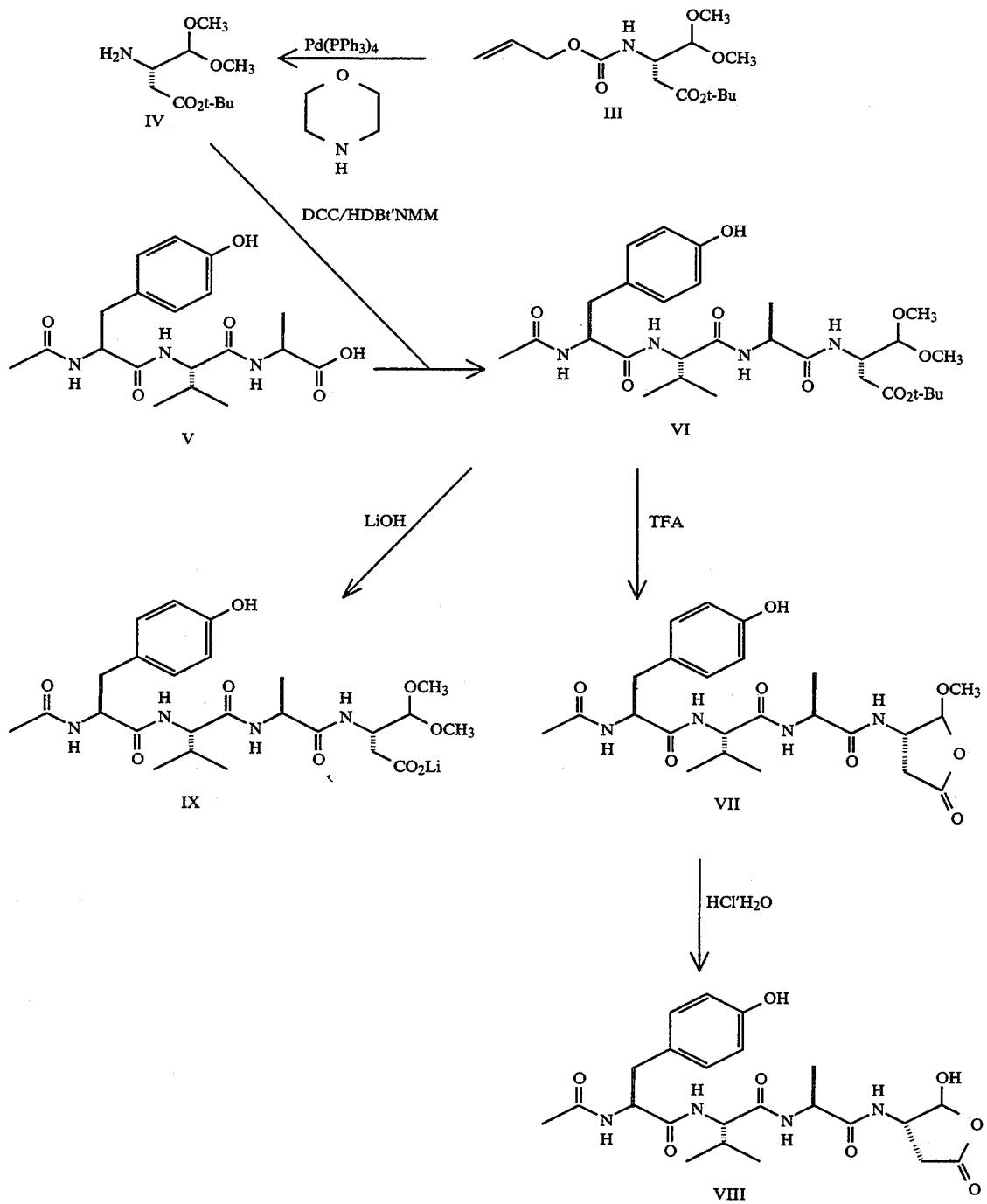

-continued
Scheme I

The reactions of Scheme I proceed as follows. A mixed anhydride of allyloxycarbonyl (Alloc)-(S)-aspartic acid β-t-butyl ester with isobutylchloroformate (IBCF) is formed in the presence of N-methylmorpholine (NMM). This anhydride is reduced to the corresponding alcohol II using sodium borohydride at 0° C. in a solvent of 4:1 tetrahydrofuran (THF):methanol. The alcohol II is then oxidized using dimethyl sulfoxide (DMSO), oxallyl chloride, and triethyl amine to the corresponding aldehyde which is protected as the dimethyl acetal using methanol, trimethyl orthoformate and p-toluenesulfonic acid to afford III. The Alloc protecting group is then removed with tetrakis triphenylphosphine palladium in the presence of morpholine to afford amine IV. This amine is then coupled to the tripeptide, N-acetyl-(S)-tyrosinyl-(S)-valinyl-(S)-alanine using dicyclohexyl carbodiimide (DCC) in the presence of hydroxybenzotriazole (HOBt), and NMM to afford VI. The t-butyl ester is then removed with neat TFA (trifluoroacetic acid) to provide the cyclic O-methylacylal VII. The final hydrolysis is accomplished with dilute hydrochloric acid in 1:1 water:methanol to give VIII. In addition, VI can be saponified with LiOH to give the dimethyl acetal IX.

Scheme II
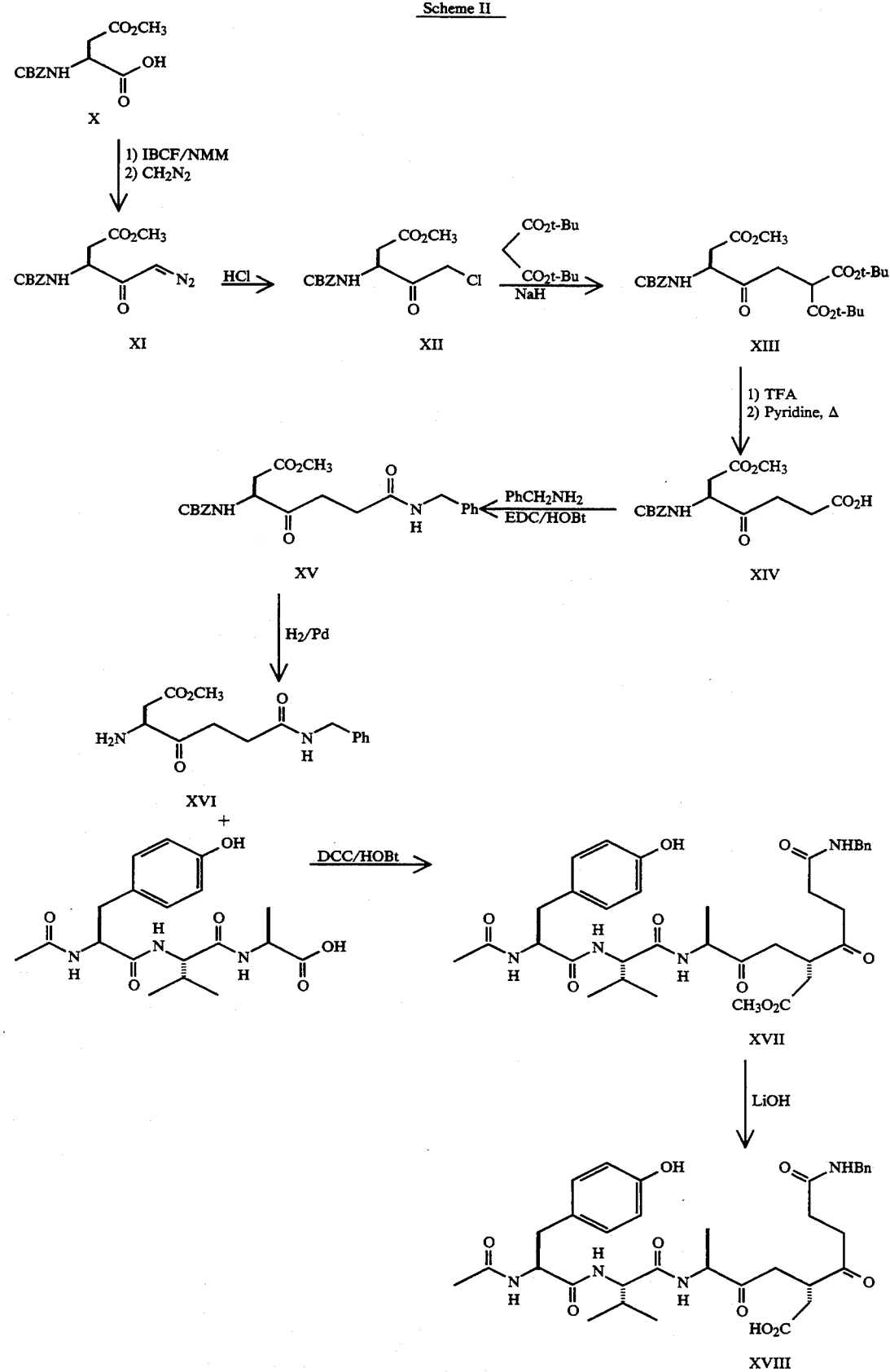
Structures such as XVIII can be prepared as shown in scheme II. N-CBZ-Aspartic acid β-methyl ester can be treated with i-butylchloroformate in the presence of N-methylmorpholine (NMM) followed by diazomethane to afford diazomethylketone XI. Treatment of XI with hydrochloric acid gives chloromethylketone XII, which can be used to alkylate the sodium salt of di-t-butyl malonate to give ketodiester XIII. The t-butyl groups can be removed with trifluoro acetic acid and the resultant dicarboxylic acid can be decarboxylated in hot pyridine to afford keto acid XIV. Acid XIV can then be coupled to benzyl amine using ethyldimethylaminopropyl carbodiimide in the presence of hydroxybenzotriazole (HOBt) to afford amide XV. Removal of the CBZ group is accomplished with hydrogen in the presence of 10% palladium on carbon to give amine XVI. This amine can then be coupled to N-acetyltyrosinyl-valinyl-alanine using dicyclohexyl carbodiimide in the presence of HOBt to afford XVII. Final deprotection of the carboxylic acid can be accomplished with lithium hydroxide to afford the desired ICE inhibitor XVIII.

The compounds of the instant invention of the formula (I), as represented in the Examples hereinunder shown to exhibit in vitro inhibitory activities with respect to interleukin-1≈. As a class, these compounds have been shown to inhibit interleukin-1S converting enzyme from cleaving precursor interleukin-1β as to form active interleukin-1β at a Ki of less than 1 uM.

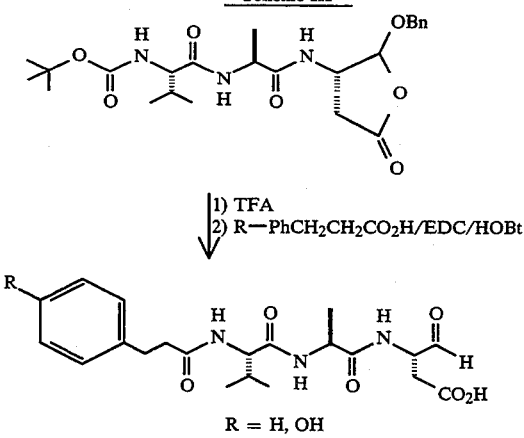

The reactions of scheme III proceed as follows. N-Allyloxycarbonyl-3-amino-4-hydroxybutanoic acid tert-butyl ester can be oxidized to the corresponding aldehyde using DMSO, oxalyl chloride and Hunig's base (Diisopropylethylamine). The aldehyde is not isolated, but converted to the O-benzylacylal by treatment with benzyl alcohol and 3 Å molecular sieves in the presence of a catalytic amount of p-toluene sulfonic acid followed by treatment with TFA (trifluoroacetic acid). The alloc protecting group is removed in the presence of BOC-Val-Ala using tributyltin hydride and (PPh$_3$)$_2$PdCl$_2$. Coupling is then effected in the same flask using EDC and HOBt. The t-butoxycarbonyl protecting group is then removed with TFA and the resulting salt coupled to either 3-phenylpropionic acid or 3-(4-phydroxyphenyl)-propionic acid using EDC, HOBt and 4-methylmorpholine. The benzyl protecting group is then removed by hydrogenolysis using Pd(OH)$_2$ on carbon as a catalyst.

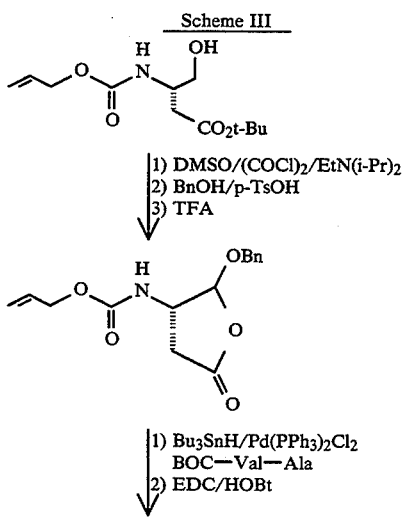

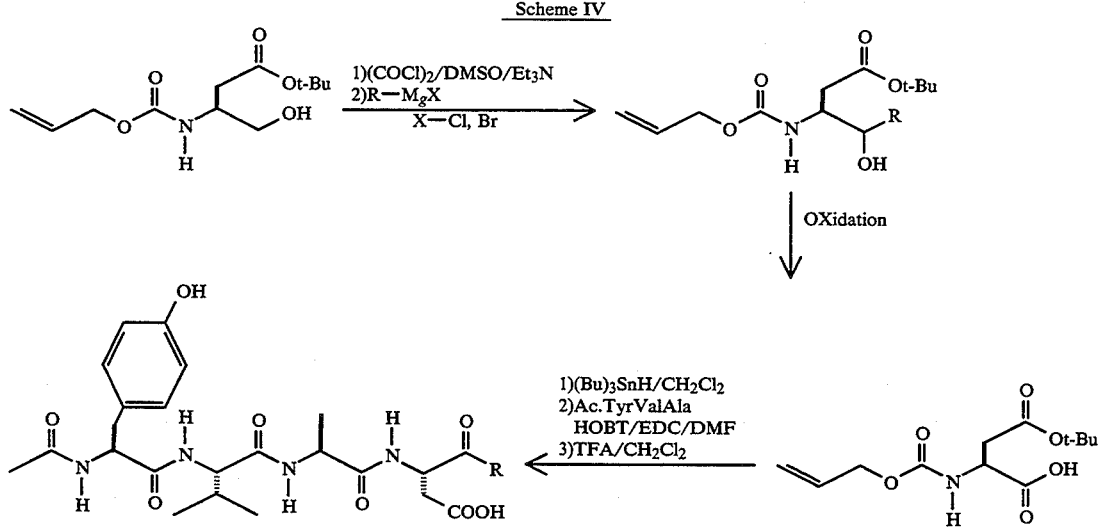

Scheme V

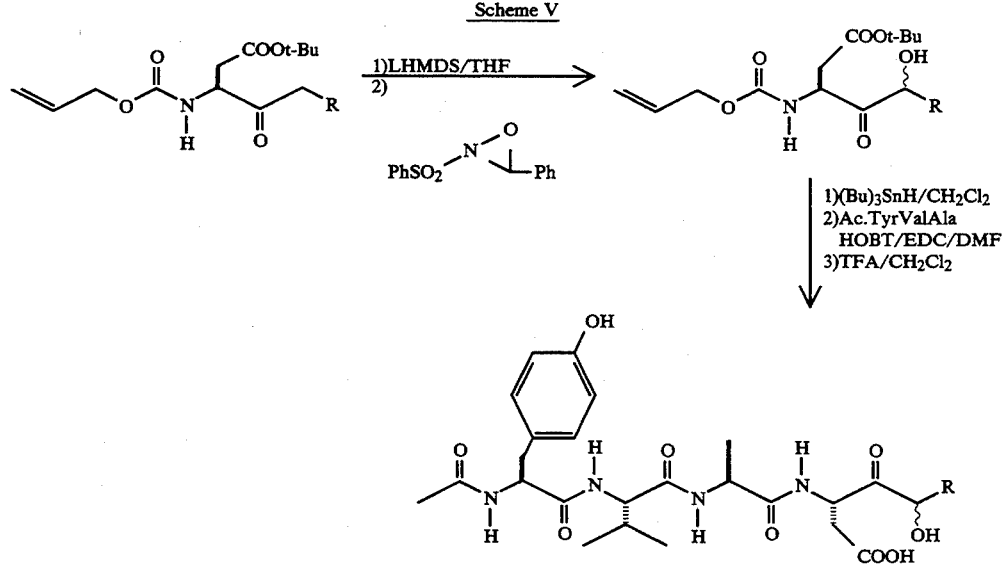

The ketones shown in Scheme IV can be prepared as follows. 3-Allyloxycarbonylamino-4-hydroxy butanoic acid t-butyl ester can be oxidized using DMSO, oxallyl chloride, and either triethyl amine or Hunig's base to form the corresponding aldehyde. Grigniard reagents can then be added to the aldehyde to afford the secondary alcohol which can then be oxidized to the corresponding ketone using DMSO, oxallyl chloride, and triethyl amine, or pyridinium dichromate, or Dess-Martin periodinane. The alloc protecting group can then be removed with palladium(O) and tributyl tin hydride, and the resulting amine coupled to carboxylic acids EDC and HOBt. Treatment with TFA gives the desired inhibitors.

The hydroxy ketones shown in Scheme V can be prepared as follows. Enolization of 3-allyloxycarbonylamino-4-oxo-7-phenylheptanoic acid t-butyl ester with lithium hexamethyldisilazide can be followed by treatment with N-phenylsulphonyl oxaziridine to give the corresponding hydroxyketone. The alloc protecting group can then be removed with palladium(O) and tributyl tin hydride, and the resulting amine coupled to carboxylic acids using EDC and HOBt. Treatment with TFA gives the desired inhibitors.

The example shown in scheme VI can be prepared as follows. Phenylpropyl bromide is treated with magnesium to form the Grigniard reagent followed by di-t-Butyloxalate to afford the corresponding α-ketoester. Treatment of the ester with DAST (Diethylamino Sulphurtrifluoride) followed by deprotection with TFA and treatment with oxalyl chloride affords the desired acid chloride. Aspattic acid β-t-butyl ester is acylated with biphenylcarbonyl chloride followed by treatment with EDC to afford the desired oxazalone. Treatment of this oxazalone with acid chloride I followed by decarboxylation with oxalic acid affords the desired difluoroketone. Reduction with sodium borohydride followed by removal of the biphenyl with sodium amalgum gives the amino alcohol. The amino alcohol is then acylated with phenylpropionyl-valinyl-alanine in the presence of EDC and HOBt and the resulting hydroxy amide oxidized to the difluoroketone with Dess-Martin periodinane and deprotected with TFA to afford the desired inhibitor.

The compounds of the instant invention of the formula (I), as represented in the Examples hereinunder shown to exhibit in vitro inhibitory activities with respect to interleukin-1β. As a class these compounds have been shown to inhibit interleukin-1β converting enzyme from cleaving precursor interleukin-1β as to form active interleukin-1β at a Ki of less than 1 uM.

Scheme VI

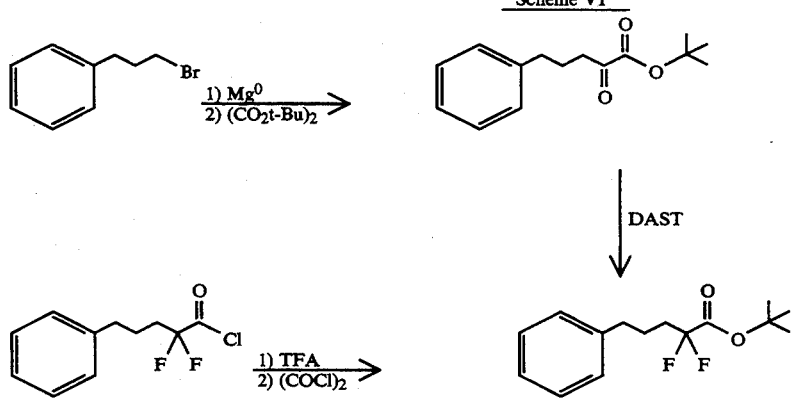

-continued
Scheme VI

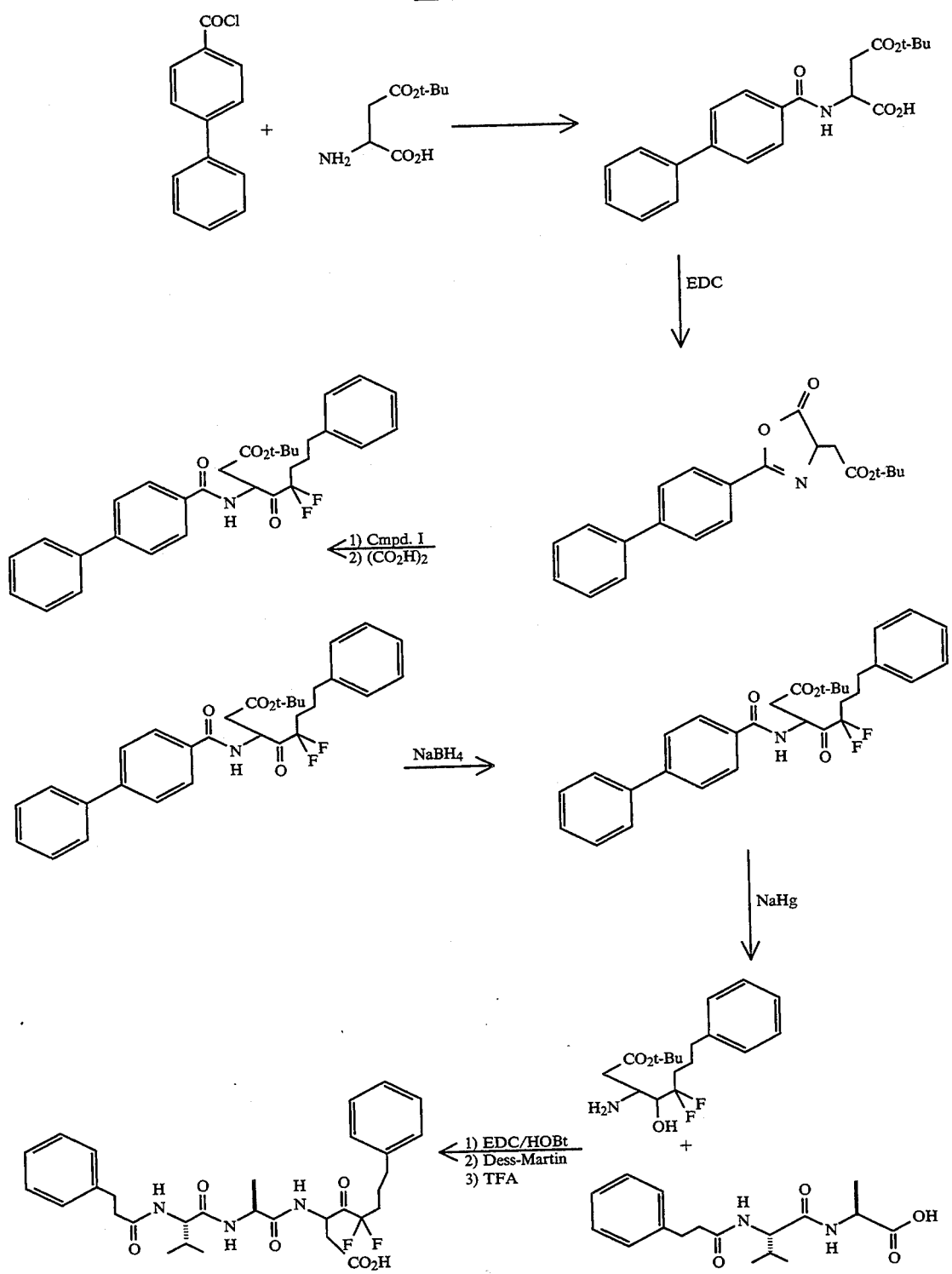

This invention also relates to a method of treatment for patients (including man and/or mammalian animals raised in the dairy, meat, or fur industries or as pets) suffering from disorders or diseases which can be attributed to IL-1/ICE as previously described, and more specifically, a method of treatment involving the administration of the IL-1/ICE inhibitors of formula (I) as the active constituents.

Accordingly, disease states in which the ICE inhibitors of Formula I may be useful as therapeutic agents include, but are not limited to, infectious diseases where active infection exists at any body site, such as meningitis and salpingitis; complications of infections including septic shock, disseminated intravascular coagulation, and/or adult respiratory distress syndrome; acute or chronic inflammation due to antigen, antibody, and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis. Immune-based diseases which may be responsive to ICE inhibitors of Formula I include but are not limited to conditions involving T-cells and/or macrophages such as acute and delayed hypersensitivity, graft rejection, and graft-versus-host-disease; auto-immune diseases including Type I diabetes mellitus and multiple sclerosis. ICE inhibitors of Formula I may also be useful in the treatment of bone and cartilage resorption as well as diseases resulting in excessive deposition of extracellular matrix such as interstitial pulmonary fibrosis, cirrhosis, systemic sclerosis, and keloid formation. ICE inhibitors of Formula I may also be useful in treatment of certain tumors which produce IL 1 as an autocrine growth factor and in preventing the cachexia associated with certain tumors.

For the treatment the above mentioned diseases, the compounds of formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intracisternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of Formula I, and as such are not intended to limit the invention as set forth in the claims appended, thereto.

EXAMPLE 1

N-(N-Acetyl-tyrosinyl-valinyl-alaninyl)-3-amino-4-oxobutanoic acid.

STEP A

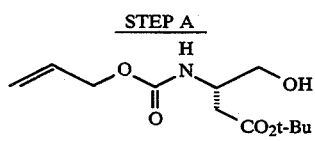

N-allyloxycarbonyl-3-amino-4-hyroxybutanoic acid tert-butyl ester.

To a solution of N-allyloxycarhonyl (S)-aspartic acid β-tert-butyl ester (2.00 g, 7.32 mmol) in 50 mL of tetrahydrofuran (THF) at 0° C., was added N-methyl morpholine (NMM, 885 mL, 8.05 mmol) followed by isobutyl chloroformate (IBCF, 997 mL, 7.68 mmol). After 15 minutes, this mixture was added to a suspension of sodium borohydride (550 mg, 14.55 mmol) in 50 mL of THF and 12.5 mL of methanol at −45° C. After 30 minutes at −45° C., the mixture was warmed to 0° C. and held at that temperature for 30 minutes. The reaction was quenched with acetic acid, diluted with 1:1 ethyl acetate:hexane, and washed 3 times with dilute sodium bicarbonate. The organics were dried over sodium sulfate, filtered, and concentrated. The residue was purified by MPLC on silica-gel (35×350 mm column, 30% ethyl acetate/hexane) to give the desired product: $^1$H NMR (200 MHz, CD$_3$OD) δ5.9 (m, 1H), 5.28 (br d, 1H, J=17 Hz), 5.15 (br d, 1H, J=9 Hz), 4.52 (br d, 2H, J=6 Hz), 3.98 (m, 1H), 3.48 (ABX, 2H, J=5, 6, 11 Hz), 2.53 (dd, 1H, J=5, 16 Hz), 2.32 (dd, 1H, J=9, 16 Hz), 1.43 (s, 9H).

STEP B

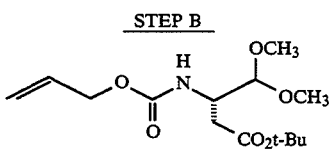

N-allyloxycarbonyl-3-amino-4-oxobutanoic acid β-tert-butyl ester dimethyl acetal.

To a solution of dimethyl sulfoxide (757 mL, 10.67 mmol) in 10 mL of dichloromethnane at −45° C. was added oxalyl chloride (508 mL, 5.82 mmol). After 5 minutes, a solution of N-allyloxycarbonyl-3-amino-4-hyroxybutanoic acid tert-butyl ester (1.25 g, 4.85 mmol) in 10 mL of dichloromethane was added. After 15 minutes, triethyl amine (2.03 mL, 14.55 mmol) was added. After 30 minutes, the mixture was warmed to −23° C. and stirred for 30 minutes. The mixture was diluted with 1:1 ethyl acetate/hexane, washed with water, 1N sodium hydrogensulfate, and twice with water. The organics were dried over sodium sulfate, filtered, and concentrated. The resultant oil was dissolved in 200 mL of methanol and 20 mL of trimethyl orthoformate and 100 mg of p-toluene sulphonic acid were added. After 16 hours, the reaction was quenched with saturated sodium bicarbonate and concentrated in vacuo. The mixture was diluted with ether and washed 5 times with dilute sodium bicarbonate. The ether layer was dried over magnesium sulfate, filtered, and concentrated to afford the title compound as a colorless oil: $^1$H NMR (200 MHz, CD$_3$OD) δ5.9 (m, 1H), 5.26 (br d, 1H, J=17 Hz), 5.14 (br d, 1H, J=10 Hz), 4.51 (br d, 2H, J=5.33 Hz), 4.25 (d, 1H, J=4.79 Hz), 4.11 (m, 1H), 3.40 (s, 3H), 3.39 (s, 3H), 2.52 (dd, 1H, J=4.86, 15.27 Hz), 2.30 (dd, 1H, J=9.00, 15.28 Hz), 1.43 (s, 9H).

STEP C

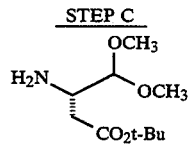

3-Amino-4-oxobutanoic acid β-tert-butyl ester dimethyl acetal.

To a solution of N-allyloxycarbonyl-3-amino-4-oxobutanoic acid β-tert-butyl ester dimethyl acetal (312 mg, 1.03 mmol) in 10 mL of THF was added morpholine (897 mL, 10.3 mmol) and tetrakis triphenylphosphine palladium (100 mg). After 3 hours, the mixture was diluted with 1:1 ethyl acetate/hexane and washed 5 times with dilute sodium bicarbonate. The organics were dried over sodium sulfate, filtered, and concentrated. The resulting oil was purified by MPLC on silica-gel (22×300 mm column, linear gradient of dichloromethane to 1% ammonia and 10% methanol in dichloromethane) to afford the title compound as a pale-yellow oil: ¹H NMR (200 MHz, CD₃OD) δ4.15 (d, 1H, J=5.67 Hz), 3.41 (s, 3H), 3.40 (s, 3H), 3.19 (m, 1H), 2.47 (dd, 1H, J=4.88, 16.06 Hz), 2.22 (dd, 1H, J=7.86, 16.16 Hz), 1.45 (s, 9H).

STEP D

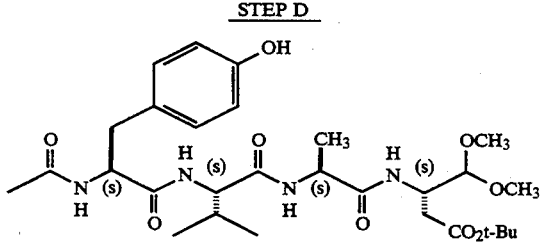

N-(N-Acetyl-tyrosinyl-valinyl-alaninyl)-3-amino-4-oxobutanoic acid β-tert-butyl ester dimethyl acetal.

To a solution of 3-Amino-4-oxobutanoic acid β-tert-butyl ester dimethyl acetal (10.4 mg, 0.473 mmol) in 3 mL of DMF at 0° C. was added N-methyl morpholine (260 mL, 2.37 mmol) followed sequentially by N-Acetyl-tyrosinyl-valinyl-alanine (229 mg, 0.473 mmol), hydroxybenzotriazole (96 mg, 0.710 mmol), and dicyclohexylcarbodiimide (98 mg, 0.473 mmol). After 24 hours at ambient temperature, the mixture was filtered and purified by SEPHADEX LH-20 chromatography (1M×50 mm column, methanol eluent). The resulting product was further purified by MPLC on silica-gel (22×300 mm column, eluting with a linear gradient of dichloromethane to 1% ammonia and 10% methanol in dichloro methane) to give the title compound as a colorless solid: ¹H NMR (200 MHz, CD₃OD) δ7.04 (br d, 2H, J=8.54 Hz), 6.67 (br d, 2H, J=8.57 Hz), 4.58 (dd, 1H, J=5.61, 9.03), 4.4–4.2 (m, 3H), 4.16 (d, 1H, J=7.12 Hz), 3.39 (s, 3H), 3.38 (s, 3H), 3.01 (dd, 1H, J=5.54, 13.97 Hz), 2.76 (dd, 1H, J=8.89, 13.90 Hz), 2.53 (dd, 1H, J=5.50, 14.45 Hz), 2.34 (dd, 1H, J=7.83, 15.49 Hz), 2.05 (m, 1H), 1.90 (s, 3H), 1.41 (s, 9H), 1.33 (d, 3H, J=7.16 Hz), 0.94 (d, 3H, J=6.73 Hz), 0.92 (d, 3H, J=6.77 Hz).

STEP E

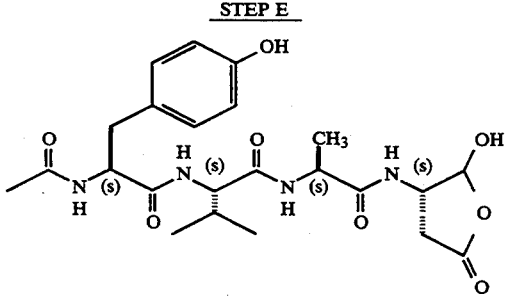

N-(N-Acetyl-tyrosinyl-valinyl-alaninyl)-3-amino-4-oxobutanoic acid.

A solution of N-(N-Acetyl-tyrosinyl-valinyl-alaninyl)-3-amino-4-oxobutanoic acid β-tert-butyl ester dimethyl acetal (17.4 mg) in 2 mL of trifluoroacetic acid was aged for 15 minutes and concentrated in vacuo. The product was dissolved in 1.0 mL of methanol and 1.0 mL of water containing 60 uL of thionyl chloride was added. After 2 hours, the pH of the solution was adjusted to around 5 with sodium acetate to afford a solution of the title compound: ¹H NMR (200 MHz, CD₃OD) δ7.08 (br d, 2H, J=8.44 Hz), 6.76 (br d, 2H, J=8.49 Hz), 4.7–4.1 (m, 4H), 4.04 (d, 1H, J=7.67 Hz), 3.05–2.40 (m, 4H), 2.05 (m, 1H), 1.96 (s, 3H), 1.35 (d, 3H, J=7.23 Hz), 0.89 (d, 6H, J=6.84 Hz).

The following additional compounds are made in an analogous manner:

N-(N-Acetyl-phenylalaninyl-valinyl-alaninyl)-3-amino-4-oxobutanoic acid;

N-(3-phenylpropionyl-valinyl-alaninyl)-3-amino-4-oxobutanoic acid; and

N-(3-(4-hydroxyphenyl)-valinyl-alaninyl)-3-amino-4-oxobutanoic acid.

EXAMPLE 2

N-(N-Acetyl-tyrosinyl-valinyl-ε-CBZ-lysinyl)-3-amino-4-oxobutanoic acid.

STEP A

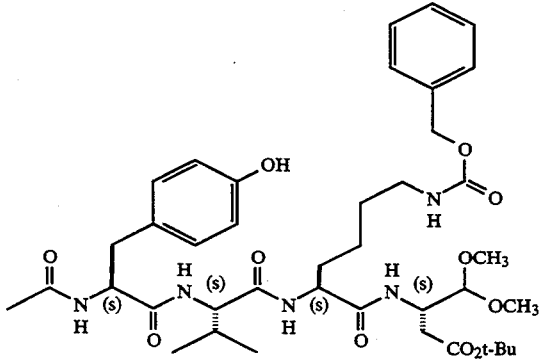

N-(N-Acetyl-tyrosinyl-valinyl-(ε-CBZ-lysinyl))-3-amino-4-oxobutanoic acid β-tert-butyl ester dimethyl acetal.

To a solution of 3-Amino-4-oxobutanoic acid β-tert-butyl ester dimethyl acetal (238 mg, 1.09 mmol) in 5 mL of DMF at 0° C. was added N-methyl morpholine (599 mL, 5.45 mmol) followed sequentially by N-Acetyl-tyrosinyl-valinyl-ε-CBZ-lysine (735 mg, 1.09 mmol), hydroxybenzotriazole (221 mg, 1.64 mmol), and dicyclohexylcarbodiimide (225 mg, 1.09 mmol). After 16 hours at ambient temperature, the mixture was filtered and purified by SEPHADEX LH-20 chromatography (1M×50 mm column, methanol eluent). The resulting product was further purified by MPLC on silica-gel (22×300 mm column, eluting with a linear gradient of dichloromethane to 1% ammoinia and 10% methanol in dichloromethane) to give the title compound as a colorless solid: ¹H NMR (200 MHz, CD₃OD) δ7.31 (br s, 5H), 7.04 (br d, 2H, J=8.35 Hz), 6.67 (br d, 2H, J=8.45 Hz), 5.04 (s, 2H), 4.61 (m, 1H), 4.44–4.25 (m, 3H), 4.17 (d, 1H, J=7.27 Hz), 3.39 (s, 3H), 3.38 (s, H), 3.1–2.9 (m, 3H), 2.75 (dd, 1H, J=9.28, 14.12 Hz), 2.53 (dd, 1H, J=5.47, 15.58 Hz), 2.33 (dd, 1H, J=7.96, 15.53 Hz), 2.04 (m, 1H), 1.88 (s, 3H), 1.8–1.2 (m, 6H), 1.41 (s, 9H), 0.94 (d, 6H, J=6.74 Hz).

STEP B

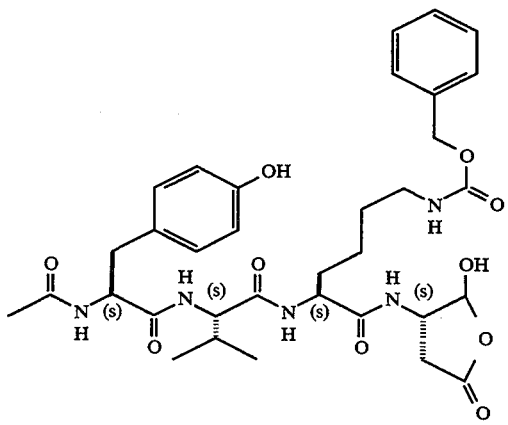

N-(N-Acetyl-tyrosinyl-valinyl-ε-CBZ-lysinyl)-3-amino-4-oxobutanoic acid.

A solution of N-(N-Acetyl-tyrosinyl-valinyl-ε-CBZ-lysinyl)-3-amino-4-oxobutanoic acid β-tert-butyl ester dimethyl acetal (14.9 mg) was treated with 1 mL of trifluoroacetic acid, aged for 15 minutes, and concentrated in vacuo. The residue was dissolved in 1.0 mL of methanol and 1.0 mL of water containing 20 uL of thionyl chloride was added. After 1 hour, the pH of the solution was adjusted to around 5 with sodium acetate to afford a solution of the title compound: 1H NMR (200 MHz, CD3OD) δ7.33 (br s, 5H), 7.05 (br d, 2H, J=8.35 Hz), 6.74 (br d, 2H, J=8.35 Hz), 4.6–3.9 (m, 5H), 3.1–2.3 (m, 6H), 1.98 (m, 1H), 1.92 (s, 3H), 1.8–1.2 (m, 6H), 0.89 (d, 6H, J=6.60 Hz).

The following additional compounds are made in an analogous manner:

N-(N-Acetyl-phenylalaninyl-valinyl-ε-CBZ-lysinyl)-3-amino-4-oxobutanoic acid; and N-(3-phenylpropionyl-valinyl-ε-CBZ-lysinyl)-3-amino-4-oxobutanoic acid;

N-(3-(4-hydroxyphenyl)-propionyl-valinyl-ε-CBZ-lysinyl)-3-amino-4-oxobutanoic acid.

EXAMPLE 3

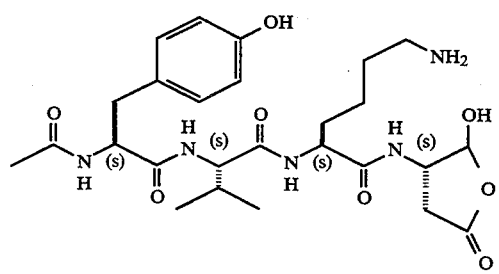

N-(N-Acetyl-tyrosinyl-valinyl-lysinyl)-3-amino-4-oxobutanoic acid.

A solution of N-(N-Acetyl-tyrosinyl-valinyl-ε-CBZ-lysinyl)-3-amino-4-oxobutanoic acid β-tert-butyl ester dimethyl acetal (16.8 mg) was dissolved in 2 mL of methanol and 10 mg of Pearlman's catalyst (Pd(OH)2 on Carbon) was added. After 30 minutes under hydrogen, the mixture was filtered and concentrated. The residue was treated with 2 mL of trifluoroacetic acid, aged for 15 minutes, and concentrated in vacuo. The product was dissolved in 1.0 mL of methanol and 1.0 μL of water containing 20 uL of thionyl chloride was added. After 1 hour, the pH of the solution was adjusted to around 5 with sodium acetate to afford a solution of the title compound: 1H NMR (200 MHz, CD3OD) δ7.10 (br d, 2H, J=8.01 Hz), 6.77 (br d, 2H, J=8.25 Hz), 4.7–4.0 (m, 5H), 3.1–2.4 (m, 6H), 2.04 (m, 1H), 1.95 (s, 3H), 1.9–1.3 (m, 6H), 0.90 (d, 6H, J=6.59 Hz).

The following additional compounds are prepared in an analogous manner:

N-(N-Acetyl-phenylalaninyl-valinyl-lysinyl)-3-amino-4-oxobutanoic acid;

N-(3-phenylpropionyl-valinyl-lysinyl)-3-amino-4-oxobutanoic acid; and

N-(3-(4-hydroxyphenyl)-propionyl-valinyl-lysinyl)-3-amino-4-oxobutanoic acid.

EXAMPLE 4

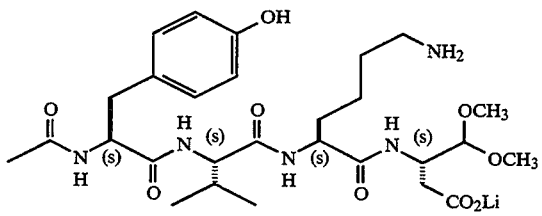

N-(N-Acetyl-tyrosinyl-valinyl-lysinyl)-3-amino-4-oxobutanoic acid dimethyl acetal lithium salt.

A solution of N-(N-Acetyl-tyrosinyl-valinyl-ε-CBZ-lysinyl)-3-amino-4-oxobutanoic acid β-tert-butyl ester dimethyl acetal (15.6 mg) was disolved in 2 mL of methanol and 10 mg of Pearlman's catalyst (Pd(OH)2 on Carbon) was added. After 30 min under hydrogen, the mixture was filtered and concentrated. The solid was dissolved in 1 mL of methanol and 1 mL of water. Lithium hydroxide hydrate (22 mg) was added. After 16 hours at ambient temperature, the mixture was concentrated in vacuo to give the title compound in the presence of lithium hydroxide: 1H NMR (200 MHz, CD3OD) δ6.88 (br d, 2H, J=8.4 Hz), 6.54 (br d, 2H, J=8.4 Hz), 4.6–4.1 (m, 5H), 3.38 (s, 6H), 3.0–2.2 (m, 6H), 2.08 (m, 1H), 1.88 (s, 3H), 1.9–1.2 (m, 6H), 0.94 (d, 6H, J=6.7 Hz), 0.91 (d, 3H, J=6.7 Hz).

EXAMPLE 5

N-(3-phenylpropionyl-valinyl-alaninyl)-3-amino-4-oxobutanoic acid

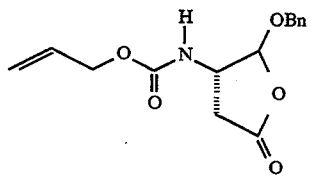

Step A

N-Allyloxycarbonyl-4-amino-5-benzyloxy-2-oxotetrahydrofuran

To a solution of dimethylsulfoxide (1.86 mL, 26.16 mmol) in 30 mL of freshly distilled dichloromethane at −45° C. was added oxalyl chloride (1.24 mL, 14.27 mmol). After 5 minutes, a solution of N-allyloxycarbonyl-3-amino-4-hydroxybutanoic acid tert-butyl ester (3.07 g, 11.89 mmol) in 20 mL of dichloromethane was added. After 15 minutes, diisopropyl ethylamine (6.21 mL, 35.67 mmol) was added and the mixture stirred at 0° C. for 30 minutes. The mixture was diluted with ethyl acetate and washed with water, 1N sodium hydrogen sulfate, and three times with water. The organics were dried over sodium sulfate, filtered, and concentrated. The resulting colorless oil was dissolved in 7 mL of dichloromethane and 6.5 mL of benzyl alcohol. To this solution was added ~1 g of 3 Å molecular sieves followed by a catalytic amount of p-toluenesulfonic acid. After 16 hours, trifluoroacetic acid (~8 mL) was added, and the mixture stirred for 30 minutes and concentrated. The mixture was diluted with ethyl acetate and filtered through CELITE. The organics were then washed three times with dilute sodium bicarbonate, dried over sodium sulfate, filtered, and concentrated. The residue was purified by MPLC on silica-gel (35×350 mm column, using 20% ether in hexane as eluent until the benzyl alcohol came off, and then 10% ethyl acetate in 1:1 dichloromethane/hexane to elute the products) to afford the title compound as a mixture of two diastereomers which crystallized on standing: $^1$H NMR (400 MHz, CD$_3$OD) δ7.3 (m, 5H, Ar—H̲), 5.89 (m, 1H, CH═CH$_2$), 5.61 (d, 0.5H, CHOBn), 5.4̲7 (d, 0.5H, CHOB̲n), 5.28 (br d, 1H, CH═CH̲H), 5.18 (br d, 1H, CH═CHH̲), 4.82 (2d's, 1H, CH$_2$Ph), 4.6̲7 (2d's, 1H, CH$_2$Ph), 4.5̲2 (m, 3H, CH$_2$OCO, C̲HN), 3.02 (dd, 0.5H, CH̲HCO$_2$), 2.74 (dd, 0.5̲H, CHH̲CO$_2$), 2.61 (dd, 0.5H, CH̲HCO$_2$), 2.45 (dd, 0.5H, CHH̲CO$_2$).

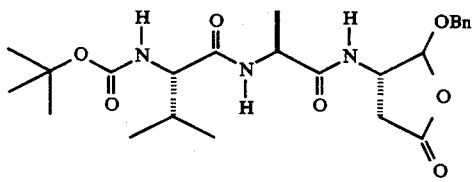

N-(Tert-butoxycarbonyl-valinyl-alaninyl)-4-amino-5-benzyloxy-2-oxotetrahydrofuran To a solution of N-allyloxycarbonyl-4-amino-5-benzyloxy-2-oxotetrahydrofuran (407.6 mg, 1.399 mmol) and tert-butoxycarbonyl-valinyl-alanine (807 mg, 2.8 mmol) in 10 mL of dichloromethane was added ~20 mg of (PPh$_3$)$_2$PdCl$_2$ followed by tri-n-butyltin hydride (415 μL, 1.54 mmol) dropwise over two minutes. An additional 100 μl of tri-n-butyltin hydride was added dropwise until the color of the reaction mixture had turned dark orange. Dimethylformamide (5 mL0 was added followed by hydroxybenzotriazole (567 mg, 4.2 mmol). The mixture was cooled to 0° C. and ethyl dimethylaminopropyl carbodiimide (295 mg, 1.54 mmol) was added. After 16 hours at ambient temperature, the mixture was diluted with ethyl acetate and washed three times with dilute hydrochloric acid, and three times with dilute sodium bicarbonate. The mixture was dried over sodium sulfate, filtered, and concentrated. The residue was purified by MPLC on silica-gel (22×300 mm column, 50% ethyl acetate in hexane as eluent) to afford 590.4 mg (91%) of the title compound as a mixture of two diastereomers: $^1$H NMR (400 MHz, CD$_3$OD) δ7.4-7.05 (m, 5H, Ar—H̲), 5.63 (d, 0.5H, CHOBn), 5.45 (d, 0.5H, CHOB̲n), 4.9-4.6 (m, 3H, CH̲$_2$Ph, CHN), 4.4-4.2 (m, 2̲H, CHN̲), 3.83 (m, 1H, CH̲N), 3.0̲3 (dd, 0.5H, CH̲HCO$_2$), 2.77 (dd, 0.5H, CH̲HCO$_2$), 2.61 (dd, 0.5H, C̲HHCO$_2$), 2.47 (dd, 0.5H, CHH̲CO$_2$), 2.01 (m, 1H, CH̲(CH$_3$)$_2$), 1.43 (s, 9H, C(CH̲$_3$)$_3$), 1.33 (d, 1.5H, CH̲CH$_3$), 1.27 (d, 1.5H, CHCH̲$_3$), 0.9 (m, 6H, CH(CH̲$_3$)$_2$).

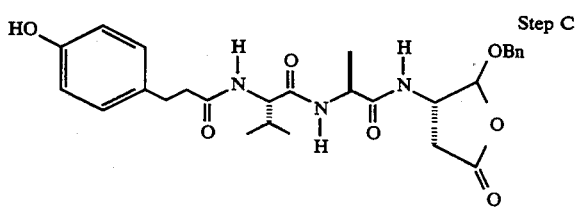

N-(3-(4-Hydroxyphenyl)-propionyl-valinyl-alaninyl)-4-amino-5-benzyloxy-2-oxotetrahydrofuran N-(Tert-butoxycarbonyl-valinyl-alaninyl)-4-amino-5-benzyloxy-2-oxotetrahydrofuran (590.4 mg) was dissolved in 15 mL of trifluoroacetic acid, aged for 15 minutes, and concentrated. The residue was dissolved in methanol, diluted with toluene and concentrated to give a colorless solid. To 202.6 mg of this solid was added 3-(4-hydroxyphenyl)-propionic acid (137 mg, 0.8245 mmol), hydroxybenzotriazole (111 mg, 0.8245 mmol), dimethyl formamide (3 mL), and 4-methylmorpholine (45 μL, 0.4122 mmol). Ethyl dimethylaminopropyl carbodiimide (83 mg, 0.433 mmol) was added and the mixture stirred for 16 hours at ambient temperature. The mixture was diluted with ethyl acetate and washed three times with 2N hydrochloric acid, and twice with dilute sodium bicarbonate. The organics were dried over sodium sulfate, filtered, and concentrated to give the title compound as a mixture of two diastereomers: $^1$H NMR (400 MHz, CD$_3$OD) δ7.4-7.2 (m, 5H, Ar—H̲), 7.01 (2d's, 2H, Ar—H̲), 6.66 (d, 2H, Ar—H̲), 4.9-4.6 (m, 2.5H, CH$_2$Ph, C̲HN), 4.4-4.2 (m, 1.5̲H, CHN̲), 4.08 (d, 0.5H, J̲=7.43 Hz, CHN̲), 4.02 (d, 0.5H, J=7.15 Hz, CH̲H, 3.03 (dd, 0.5H, J̲=8.25, 18.31 Hz, CH̲HCO$_2$), 2.9̲-2.7 (m, 2.5H, CHH̲CO$_2$, CH$_2$CON), 2.60 (dd, 0.5H, J=10.19, 17.29̲ Hz, CH̲HCO$_2$), 2.55-2.45 (m, 2.5H, CHHCO$_2$, CH$_2$CH$_2$p—H̲OPh), 1.97 (m, 1H, CH(CH$_3$)$_2$), 1̲.32 (d, 1.5H, J̲=7.14 Hz, CHCH̲$_3$), 1.26 (d̲, 1.5H, J=7.14 Hz, CHCH̲$_3$), 0.9-0.8 (m, 6H̲, CH(CH̲$_3$)$_2$).

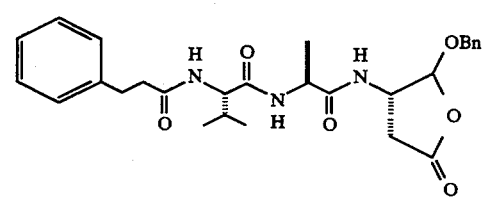

N-(3-Phenylpropionyl-valinyl-alaninyl)-4-amino-5-benzyloxy-2-oxotetrahydrofuran

N-(Tert-butoxycarbonyl-valinyl-alaninyl)-4-amino-5-benzyloxy-2-oxotetrahydrofuran (590.4 mg) was dissolved in 15 mL of trifluoroacetic acid, aged for 15 minutes, and concentrated. The residue was dissolved in methanol, diluted with toluene and concentrated to give a colorless solid. To 201.9 mg of this solid was added 3-phenylpropionic acid (123 mg, 0. 8216 mmol), hydroxybenzotriazole (111 mg, 0.8216 mmol), dimethyl formamide (3 mL), and 4-methylmorpholine (45 μl, 0.4108 mmol). Ethyl dimethylaminopropyl carbodiimide (83 mg, 0.4313 mmol) was added and the mixture stirred for 16 hours at ambient temperature. The mixture was diluted with ethyl acetate and washed three times with 2N hydrochloric acid, and twice with dilute sodium bicarbonate. The organics were dried over sodium sulfate, filtered and concentrated to give the title compound as a mixture of two diastereomers: ¹H NMR (400 MHz, CD₃OD) δ7.4–7.1 (m, 10H, Ar—H), 5.63 (d, 0.5H, J=5.03 Hz, CHOBn), 5.45 (d, 0.5H, J=1.20 Hz, CHOBn), 4.95–4.6 (m, 2.5H, CH₂Ph, CHN), 4.4–4.2 (m, 1.5H, CHN), 4.08 (d, 0.5H, J=7.38 Hz, CHN), 4.03 (d, 0.5H, J=7.15 Hz, CH N), 3.03 (dd, 0.5H, J=8.11, 18.3 Hz, CHHCO₂), 2.89 (dd, 2H, J=5.49, 8.79 Hz, CH₂CON), 2.76 (dd, 0.5H, J=8.76, 17.38 Hz, CHHCO₂), 2.7–2.4 (m, 3H, CHHCO₂, CH₂CH₂Ph), 1.98 (m, 1H, CH(CH₃)₂), 1.31 (d, 1.5H, CHCH₃), 1.25 (d, 1.5H, CHCH₃), 0.87 (m, 6H, CH(CH₃)₂.

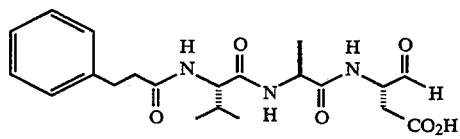

Step E

N-(3-Phenylpropionyl-valinyl-alaninyl)-3-amino-4-oxobutanoic acid

To a solution of 188 mg of N-(3-phenylpropionyl-valinyl-alaninyl)-4-amino-5-benzyloxy-2-oxo-tetrahydrofuran in 2 mL of dimethylformamide and 3 mL of methanol was added ~100 mg of Pd(OH)₂ on carbon. After the mixture had been stirred vigorously under hydrogen for 3 hours, the mixture was filtered through a 0.22 μm nylon membrane filter and concentrated. The residue was purified by MPLC on silica-gel (22×300 mm column, eluted with a gradient of dichloromethane to 8% formic acid and 32% methanol in dichloromethane) to afford 112 mg of the title compound as a colorless solid: ¹H NMR (400 MHz, CD₃OD (1:1 mixture of diastereomeric hemiacetals in this solvent)) δ7.3–7.1 (m, 5H, Ar—H), 4.58 (d, 0.5H, J=4.06 Hz, CH(OH)-(OCD₃)), 4.56 (d, 0.5H, J=3.96 Hz, CH(OH)(OCD₃)), 4.34 (m, 1H, CHN), 4.24 (m, 1H, CHN), 4.02 (d, 1H, J=7.38 Hz, CHN), 2.91 (t, 2H, J=7.61Hz, CH₂CON), 2.7–2.4 (m, 4H, CH₂Ph, CH₂CO₂), 2.00 (m, 1H, CH(CH₃)₂), 1.32 (d, 3H, J=7.10 Hz, CHCH₃), 0.88 (d, 3H, J=6.82 Hz, CH(CH₃)₂), 0.85 (d, 3H, J=6.83 Hz, CH(CH₃)₂).

The following additional compounds can be prepared by the same procedures as exemplified above:
(a) N-(N-acetyl-tyrosinyl-valinyl-(N,N)-dimethyl-Lisinyl)-3-amino-4-oxo-butanoic acid;
(b) N-(N-phenylpropionyl)valinyl-glycinyl)-3-amino-4-oxo-butanoic acid;
(c) N(N-acetyl-alaninyl)-3-amino-4-oxo-butanoic acid;
(d) N-(N-acetyl-valinyl-alaninyl)-3-amino-4-oxo-butanoic acid;
(e) N-propionyl-3-amino-4-oxo-butanoic acid;
(f) N-(N-acetyl-3-amino-4-oxo-butanoic acid; or
(g) N-(N-Acetyl tyrosinyl-valinyl-histidinyl-3-amino-4-oxo butanac acid.

EXAMPLE 6

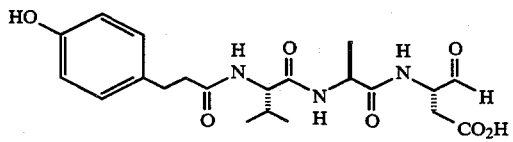

N-(3-(4-Hydroxyphenyl)propionyl-valinyl-alaninyl)-3-amino-4-oxobutanoic acid

To a solution of 195 mg of N-(3-(4-hydroxyphenyl)-propionyl-valinyl-alaninyl)-4-amino-5-benzyloxy-2-oxotetrahydrofuran in 5 mL of methanol was added ~100 mg of Pd(OH)₂ on carbon. After the mixture had been stirred vigorously under hydrogen for 3 hours, the mixture was filtered through a 0.22 μm nylon membrane filter and concentrated. The residue was purified by MPLC on silica-gel (22×300 mm column, eluted with a gradient of dichloromethane to 8% formic acid and 32% methanol in dichloromethane) to afford 115 mg of the title compound as a colorless solid: ¹H NMR (400 MHz, CD₃OD (1:1 mixture of diastereomeric hemiacetals in this solvent)) δ7.01 (d, 2H, J=8.39 Hz, Ar—H), 6.67 (d, 2H, J=8.53 Hz, Ar—H), 4.58 (d, 0.5H, J=3.92 Hz, CH(OH)(OCD₃)), 4.56 (d, 0.5H, J=4.06 Hz, CH(OH)(OCD₃)), 4.34 (m, 1H, CHN), 4.24 (m, 1H, CHN), 4.09 (d, 1H, J=7.10 Hz, CHN), 2.81 (t, 2H, J=7.56 Hz, CH₂CON), 2.7–2.4 (m, 4H, CH2Ar, CH₂CO₂), 2.00 (m, 1H, CH(CH₃)₂), 1.32 (d, 3H, J=5.81Hz, CHCH₃), 0.89 (d, 3H, J=6.82 Hz, CH(CH₃)₂), 0.85 (d, 3H, J=6.87 Hz, CH(CH₃)₂).

EXAMPLE 7

N-(3-Phenylpropionyl-Valinyl-Alaninyl)3-amino-4-oxo-5-phenylpentanoic acid.

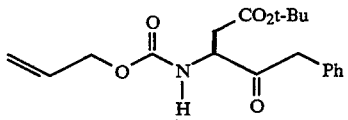

Step A

3-Allyloxycarbonylamino-4-oxo-5-phenylpentanoic acid t-butyl ester.

2M Oxallylchloride (0.89 mL) in CH₂Cl₂ was added to a mixture of DMSO (0.137 mL, 1.78 mmol) in CH₂Cl₂ (2 mL) at −78° C. The resulting mixture was stirred at −78° C. for 10 min and the N-alloc-b-t-butyl aspartic alcohol (420 mg. 1.615 mmol) in CH₂Cl₂ (4 mL) was added dropwise. The mixture was stirred at −78° C. for 30 min and 5 min at −20° C. The mixture was cooled to −78° C. and i-Pr₂NEt (0.843 mL, 4.845 mmol) was added dropwise. The resulting mixture was stirred at −78° C. for 20 min and at 0° C. for 30 min. The mixture was cooled to −78° C. and (2.84 mL, 5.65 mmol) benzylmagnesium bromide was added dropwise. The mixture was stirred at −78° C. for 30 min and at 0° C. for 1 h. Et₂O (100 mL) was added and the two layers were separated. The aqueous layer was further extracted with Et₂O (3×30 mL) and the combined organic extracts were dried over Na₂SO₄. The solvent was reduced in vacuo. The residue was chromatographed over silica (1:1, Et₂O:Hexane) to provide the alcohol (350 mg, 63%). The alcohol (100 mg, 0.286 mmol) was dissolved in CH₂Cl₂ (5 mL) and Dess-Martin reagent (180 mg, 0.429 mmol) was added. The resulting mixture was stirred for 30 min at rt and the mixture was filtered through a block of silica (2:1, Hexane:Et₂O) to provide the benzylketone (75 mg, 75%).

¹H NMR (CDCl₃) δ7.3 (m, 2H), 7.15 (d, 2H), 5.88 (m, 2H), 5.25 (dd, 2H), 4.44 (m, 3H), 3.85 (s, 2H), 2.9 (dd, 1H), 2.68 (dd, 2H), 1.4 (s, 9H).

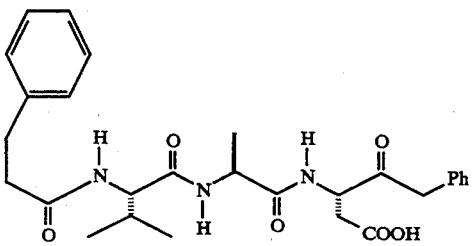

N-(3-Phenylpropionyl-Valinyl-Alaninyl)3-amino-4-oxo-5-phenylpentanoic acid.

3-Allyloxycarbonylamino-4-oxo-5-phenylpentanoic acid t-butyl ester (25 mg, 0.0717 mmol) was dissolved in CH₂Cl₂ (2 mL). PdCl₂ (Ph₃P)₂ (cat.) and Bu₃SnH (30 μl) was added dropwise. The mixture was stirred for under N₂ for 10 min. DMF (4 mL), N-phenylpropionyl-Val-Ala (31.6 mg), HOBT (29 mg) and EDC (16.4 mg) were added respectively. The resulting mixture was stirred overnight. EtOAc (20 mL) was added and the mixture was washed with aq. NaHCO₃ (5 mL). The solvent was reduced in vacuum and the residue was chromatographed over silica (95:5, CH₂Cl₂:MeOH) to afford the tetra-peptide which was dissolved in a 1:1 mixture of CH₂Cl₂/TFA (4 mL). The mixture was stirred at room temperature for 10 min and the was reduced in vacuo. The residue was recrystilized from acetone/hexane to provide the acid (42 mg).

¹H NMR (CD₃OD), δ7.2 (m, 10H), 4.62 (t, 1H), 4.35 (m, 1H), 4.12 (d, 1H), 3.85 (d, 2H), 2.88 (m, 3H), 2.72 (dd, 1H), 2.55 (m, 2H), 2.0 (m, 1H), 1.35 (d, 3H), 0.88 (dd, 6H).

EXAMPLE 8

N-(3-Phenylpropionyl-Valinyl-Alaninyl)3-amino-4-oxo-6-phenylhexanoic acid:

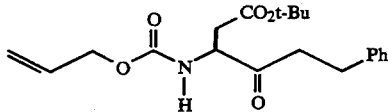

Step A

3-Allyloxycarbonylamino-4-oxo-6-phenylhexanoic acid t-butyl ester:

2M Oxallylchloride (0.975 mL) in CH₂Cl₂ was added to a mixture of DMSO (0.15 mL) in CH₂Cl₂ (2 mL) at −78° C. The resulting mixture was stirred at −78° C. for 10 min and the N-alloc-b-t-butyl aspartic alcohol (460 mg. 1.77 mmol) in CH₂Cl₂ (4 mL) was added dropwise. The mixture was stirred at −78° C. for 30 min and 5 min at −20° C. The mixture was cooled to −78° C. and i-Pr₂NEt (0.923 mL) was added dropwise. The resulting mixture was stirred at −78° C. for 20 min and at 0° C. for 30 min. The mixture was cooled to −78° C. and (2.84 mL, 5.65 mmoL) phenylethylmagnesium bromide was added dropwise. The mixture was stirred at −78° C. for 30 min and at 0° C. for 1 h Et₂O (100 mL) was added and the two layers were separated. The aqueous layer was further extracted with Et₂O (3×30 mL) and the combined organic extracts were dried over Na₂SO₄. The solvent was reduced in vacuo. The residue was chromatographed over silica (1:1, Et₂O:Hexane) to provide the alcohol (450 mg, 71%). The alcohol was dissolved in CH₃CN (3 mL) and 4A°MS (622 mg), NMO (218 mg) and 10 mol % TPAP (Tetra propyl amonium perrhuthenate). The resulting mixture was stirred for 30 min at room temperature and the mixture was filtered through a block of silica (2:1,Hexane:Et₂O) to provide the phenylethyl ketone (400 mg, 89%)

¹HNMR (CDCl₃), δ7.2 (m, 5H), 5.85 (m, 2H), 5.25 (dd, 2H), 4.55 (d, 2H), 4.4 (m, 1H), 2.88 (m, 5H), 2.65 (dd, 1H), 1.38 (s, 9H).

Step B

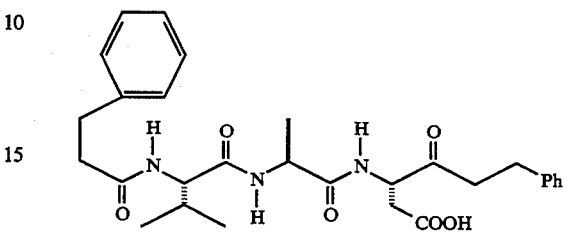

N-(3-phenylpropionyl-Valinyl-Alaninyl)3-amino-4-oxo-6-phenylhexanoic acid:

3-Allyloxycarbonylamino-4-oxo-6-phenylhexanoic acid t-butyl ester (170 mg, 0.472 mmol) was dissolved in CH₂Cl₂ (6 mL). PdCl₂(Ph₃P)₂ (cat.) and Bu₃SnH (0.194 ml) was added dropwise the mixture was stirred for under N₂ for 10 min. DMF (12 mL), N-phenylpropionyl Val Ala (205 mg), HOBT (191 mg) and EDC (108 mg) were added respectively. The resulting mixture was stirred overnight. EtOAc (200 mL) was added and the mixture was washed with aq. NaHCO₃ (20 mL). The solvent was reduced in vacuo and the residue was chromatographed over silica (95:5, CH₂Cl₂:MeOH) to afford the tetra-peptide which was dissolved in a 1:1 mixture of CH₂Cl₂/TFA (10 mL). The mixture was stirred at room temperature for 10 min and the was reduced in vacuum. The residue was recrystilized from acetone/hexane to provide the acid (205 mg).

¹H NMR (CD₃OD), δ7.2 (m, 10H). 4.6 (t, 1H), 4.32 (q, 1H), 4.09 (d, 1H), 2.92–2.75 (m, 7H), 2.72 (dd, 1H), 2.55 (m, 2H), 1.95 (m, 1H), 1.32 (d, 3H), 0.86 (dd, 6H).

EXAMPLE 9

N-(3-Phenylpropionyl-Valinyl-Alaninyl)3-amino-4-oxo-7-phenylheptanoic acid:

Step A

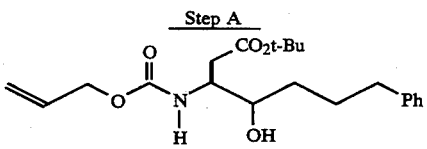

3-Allyloxycarbonylamino-4-hydroxy-7-phenylheptanoic acid t-butyl ester.

2M Oxallylchloride (2.75 mL) in CH₂Cl₂ was added to a mixture of DMSO (0.424 mL)) in CH₂Cl₂ (5 mL) at −78° C. The resulting mixture was stirred at −78° C. for 10 min and the N-alloc-b-t-butyl aspartic alcohol (1.3 g, 5.0 mmol) in CH₂Cl₂ (10 mL) was added dropwise. The mixture was stirred at −78° C. for 30 min and 5 min at −20° C. The mixture was cooled to −78° C. and i-Pr₂NEt (2.6 mL) was added dropwise. The resulting mixture was stirred at −78° C. for 20 min and at 0° C. for 30 min. The mixture was cooled to −78° C. and (8.7 mL) 2M phenylpropylmagnesium bromide in Et₂O was added dropwise. The mixture was stirred at −78° C. for 30 min and at 0° C. for 1 h. Et₂O (200 mL) was added and the two layers were separated. The aqueous layer was further extracted with Et₂O (3×60 mL) and the combined organic extracts were dried over Na₂SO₄. The solvent was reduced in vacuo. The residue was chromatographed over silica (1:1, Et₂O:Hexane) to provide the alcohol (1.6 g, 86%).

¹H NMR (CDCl₃), δ7.2 (m, 5H), 5.9 (m, 2H), 5.25 (m, 2H), 4.55 (d, 2H), 3.9 (m, 1H), 3.68 (m, 2H), 2.6 (m, 4H), 1.95–1.46 (m, 4H), 1.4 (s, 9H).

Step B

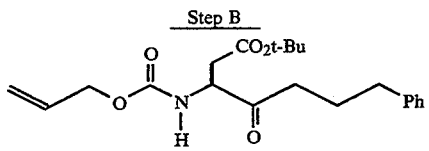

3-Allyloxycarbonylamino-4-oxo-7-phenylheptanoic acid t-butyl ester:

The alcohol (1.1 g, 3.17 mmol) was dissolved in CH₃CN (7 mL) and 4A°MS (1.858 g), NMO (556 mg) and TPAP (56 mg, 10 mol %) was added. The resulting mixture was stirred for 30 min at room temperature and the mixture was filtered through a block of silica (2:1, Hexane:Et₂O) to provide the phenylpropyl ketone (820 mg, 75%).

¹H NMR (CDCl₃) δ7.25 (m, 2H), 7.15 (m, 3H), 5.88 (m, 2H), 5.25 (dd, 2H), 4.55 (d, 2H), 4.38 (m, 1H), 2.85 (dd, 1H), 2.6 (m, 5H), 1.0 (m, 2H), 1.41 (S, 9H).

Step C

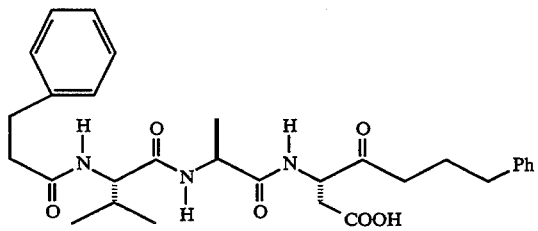

N-(3-Phenylpropionyl-Valinyl-Alaninyl)3-amino-4-oxo-7-phenylheptanoic acid:

3-Allyloxycarbonylamino-4-oxo-7-phenylheptanoic acid t-butyl ester (300 mg, 0.81 mmol) was dissolved in CH₂Cl₂ (10 mL). PdCl₂(Ph₃P)₂ (cat.) and Bu₃SnH (0.331 mmol) ml) was added dropwise. The mixture was stirred for under N₂ for 10 min. DMF (20 mL), N-phenylpropionyl Val Ala (350 mg), HOBT (326 mg) and EDC (184 mg) were added respectively. The resulting mixture was stirred overnight. EtOAc (250 mL) was added and the mixture was washed with aq. NaHCO₃ (25 mL). The solvent was reduced in vaccum and the residue was chromatographed over silica (95:5, CH₂Cl₂:MeOH) to afford the tetra-peptide which was dissolved in a 1:1 mixture of CH₂Cl₂/TFA (15 mL). The mixture was stirred at rt for 10 min and the was reduced in vacuo. The residue was recrystilized from acetone/hexane to provide the acid (420 mg)

¹H NMR (CD₃OD), δ7.2 (m, 10H). 4.6 (t, 1H), 4.32 (q, 1H), 4.12 (d, 1H), 2.91.–2.42 (m, 10H), 2.1 (m, 1H), 1.82 (m, 2H), 1.32 (d, 3H), 0.89 (dd, 6H).

EXAMPLE 10

N-(N-AcetylTyrosinyl-Valinyl-Alaninyl)-3-amino-4-oxo-7-phenyl heptanoic acid:

Step A

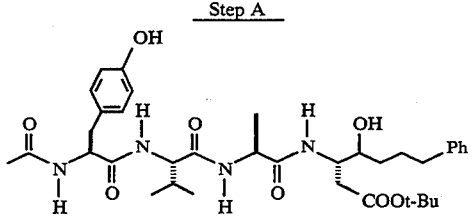

N-(N-AcetylTyrosinyl-Valinyl-Alaninyl)-3-amino-4-hydroxy-7-phenyl heptanoic acid t-butyl ester:

3-Allyloxycarbonylamino-4-oxo-7-phenylheptanoic acid t-butyl ester (155 mg, 0.41 mmol) was dissolved in CH₂Cl₂ (4 mL). PdCl₂(Ph₃P)₂ (cat.) and Bu₃SnH (0.14 mL) was added dropwise. The mixture was stirred for under N₂ for 10 min. DMF (8 mL), AcTyr.Val Ala (214 mg), HOBT (162 mg) and EDC (86.6 mg) were added respectively. The resulting mixture was stirred overnight. EtOAc (150 mL) was added and the mixture was washed with aq. NaHCO₃ (15 mL). The solvent was reduced in vacuo and the residue was chromatographed over silica (95:5, CH₂Cl₂:MeOH) to afford the tetra-peptide which was dissolved in a 1:1

¹H NMR (CD₃OD), δ7.25–7.2 (m, 5H), 7.05 (d, 2H), 6.68 (d, 2H), 4.58 (m, 1H), 4.32 (m, 1H), 4.22 (m, 1H), 4.12 (d, 1H), 3.63 (m, 1H), 3.0 (m, 1H), 2.8 (m, 1H), 2.6 (m, 2H), 2,4 (m, 1H), 2.05 (m, 1H), 1.91 (s, 3H), 1.7 (m, 2H), 1.42 (s, 9H), 1.3 (d, 3H), 0.95 (t, 6H).

Step B

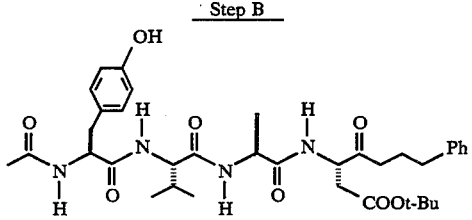

N-(N-AcetylTyrosinyl-Valinyl-Alaninyl)-3-amino-4-oxo-7-phenyl heptanoic acid t-butyl ester:

N-(N-Acetyl-Tyrosinyl-Valinyl-Alaninyl)-3-amino-4-hydroxy-7-phenyl heptanoic acid t-butyl ester (166 mg, 0.0991 mmol), was dissolved in CH₂Cl₂ (5 mL) and PDC (56 mg, 0.149 mmoL), was added. The resulting mixture was stirred at rt for 6h. The mixture was filtered through Celite and the solvent was concentrated in vacuo. The residue was chromatographed over silica (95:5, CH₂Cl₂:MeOH) to provide the ketone (28 mg) and S.M (33 mg).

¹H NMR (CD₃OD), δ7.25 (m, 2H), 7.15 (m, 3H), 7.04 (d, 2H), 6.68 (d, 2H), 4.45 (m, 2H), 4.3 (m, 1H), 4.12 (d, 1H), 2.78 (m, 2H), 2.6 (m, 4H), 2.07 (m, 1H), 1.9 (s, 3H), 1.85 (m, 2H), 1.42 (s, 9H), 1.35 (d, 3H), 0.95 (t, 3H).

Step C

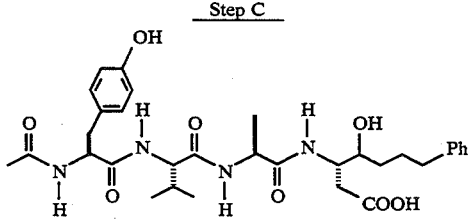

N-(N-AcetylTyrosinyl-Valinyl-Alaninyl)-3-amino-4-oxo-7-phenyl heptanoic acid:

N-(N-AcetylTyrosinyl-Valinyl-Alaninyl)-3-amino-4-oxo-7-phenyl heptanoic acid t-butyl ester (12 mg) was stirred with MeOH (0.5 mL), water(0.2 mL), and 2N NaOH (0.1 mL) overnight. The mixture was acidified with 2N HCl and was extracted with EtOAc (3×5 mL). The solvent was evaporated and the product was recrystilized from acetone/hexane to provide the title compound (8 mg).

$^1$H NMR (CD$_3$OD), δ7.25 (m, 2H), 7.15 (m, 3H), 7.04 (d, 2H), 6.68 (d, 2H), 4.55 (m, 2H), 4.3 (m, 1H), 4.15 (m, 1H), 3.0 (m, 1H), 2.85–2.48 (m, 5H), 2.05 (m, 1H), 1.9 (s, 3H), 1.83 (m, 2H), 1.35 (dd, 3H), 0.93 (t, 3H).
M/z (M+Na)+=633.5, 611.7, 595.7, 541.8, 509.9, 485.9, 441.2, 406.3, 376.2, 305.2, 249.9, 235.8, 205.9

EXAMPLE 11

N-(N-AcetylTyrosinyl-Valinyl-Alaninyl)-3-amino-4-oxo-8-phenyl octanoic acid:

Step A

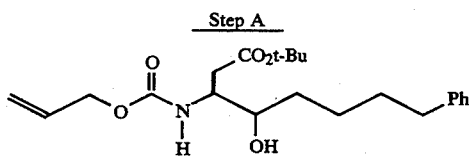

3-Allyloxycarbonylamino-4-hydroxy-8-phenyloctanoic acid t-butyl ester:

2M Oxallylchloride (0.952 mL) in CH$_2$Cl$_2$ was added to a mixture of DMSO (0.145 mL)) in CH$_2$Cl$_2$ (2 mL) at −78° C. The resulting mixture was stirred at −78° C. for 10 min and the N-alloc-b-t-butyl aspartic alcohol (450 mg, 1.74 mmol) in CH$_2$Cl$_2$ (3 mL) was added dropwise. The mixture was stirred at −78° C. for 30 min and 5 min at −20° C. The mixture was cooled to −78° C. and i-Pr$_2$NEt (0.89 mL) was added dropwise. The resulting mixture was stirred at −78° C. for 20 min and at 0° C. for 30 min. The mixture was cooled to −78° C. and (6.1 mL) 1M phenylbutyl magnesium bromide in Et$_2$O was added dropwise. The mixture was stirred at −78° C. for 30 min and at 0° C. for 1 h. Et$_2$O (30 mL) was added and the two layers were separated. The aqueous layer was further extracted with Et$_2$O (3×20 mL) and the combined organic extracts were dried over Na$_2$SO$_4$. The solvent was reduced in vacuo. The residue was chromatographed over silica (1:1, Et$_2$O:Hexane) to provide the alcohol (620 mg, 90%).

$^1$H NMR (CDCl$_3$), δ7.25 (m, 2H), 7.15 (m, 2H), 5.9 (m, 1H), 5.3 (m, 2H), 5.18 (d, 1H), 4.55 (d, 2H), 3.9 (m, 1H), 3.75 (m, 2H), 2.55 (m, 6H), 1.6 (m, 4H), 1.45 (s, 9H), 1.35 (m, 2H).

Step B

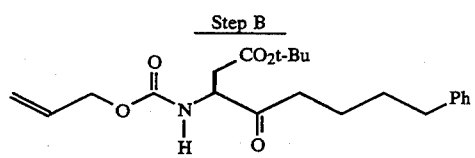

3-Allyloxycarbonylamino-4-oxo-8-phenyloctanoic acid t-butyl ester:

2M Oxallylchloride (0.73 mL) in CH$_2$Cl$_2$ was added to a mixture of DMSO (0.138 mL)) in CH$_2$Cl$_2$ (4 mL) at −78° C. The resulting mixture was stirred at −78° C. for 10 min and 3-Allyloxycarbonylamino-4-hydroxy-8-phenyloctanoic acid t-butyl ester (370 mg, 0.974 mmol) in CH$_2$Cl$_2$ (8mL) was added dropwise. The mixture was stirred at −78° C. for 30 min and 5 min at −20° C. The mixture was cooled to −78° C. and i-Pr$_2$NEt (0.85 mL) was added dropwise. The resulting mixture was stirred at −78° C. for 20 min and at 0° C. for 30 min. Et$_2$O (30 mL) was added and the two layers were separated. The aqueous layer was further extracted with Et$_2$O (3×20 mL) and the combined organic extracts were dried over Na$_2$SO$_4$. The solvent was reduced in vacuo. The residue was chromatographed over silica (1:1, Et$_2$O:Hexane) to provide the alcohol (320 mg, 87%).

$^1$H NMR (CDCl$_3$), δ7.25 (m, 2H), 7.15 (m, 2H), 5.9 (m, 1H), 5.82 (d, 1H), 5.28 (dd, 2H), 4.58 (d, 2H), 4.39 (m, 1H), 2.88 (dd, 1H), 2.65 (66, 1H), 2.55 (m, 4H), 1.6 (m, 4H), 1.45 (s, 9H).

Step C

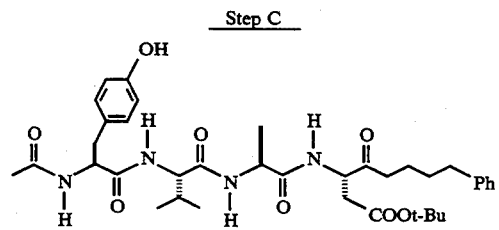

N-(N-AcetylTyrosinyl-Valinyl-Alaninyl)-3-amino-4-oxo-8-phenyl octanoic acid t-butyl ester:

3-Allyloxycarbonyl-amino-4-oxo-8-phenyloctanoic acid t-butyl ester (100 mg, 0.26 mmol) was dissolved in CH$_2$Cl$_2$ (2 mL). PdCl$_2$(Ph$_3$P)$_2$ (cat.) and Bu$_3$SnH (0.107 mL) was added dropwise. The mixture was stirred for under N$_2$ for 10 min. DMF (6 mL), AcTyr.Val Ala (252 mg), HOBT (52.7 mg) and EDC (62 mg) were added respectively. The resulting mixture was stirred overnight. EtOAc (100 mL) was added and the mixture was washed with aq. NaHCO$_3$ (10 mL). The solvent was reduced in vacuo and the residue was chromatographed over silica (95:5, CH$_2$Cl$_2$:MeOH) to afford the tetrapeptide (155 mg).

$^1$H NMR (CD$_3$OD), δ7.25 (m, 2H), 7.15 (m, 3H), 7.05 (d, 2H), 6.7 (d. 2H), 4.58 (m, 2H), 4.32 (m, 1H), 4.17 (d, 1H), 3.02 (m, 1H), 2.78 (m, 2H), 2.6 (m, 5H), 2.05 (m, 1H), 1.91 (s, 3H), 1.58 (m, 4H), 1.44 (s, 9H), 1.38 (d, 3H), 0.92 (m, 6H).

Step D

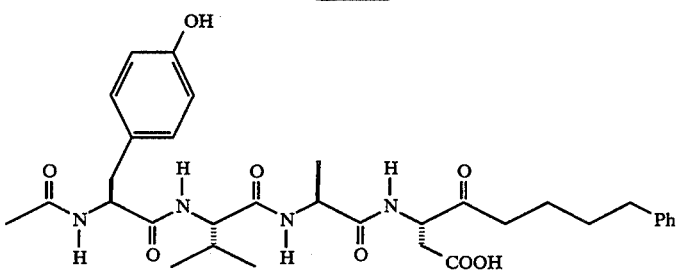

N-(N-AcetylTyrosinyl-Valinyl-Alaninyl)-3-amino-4-oxo-8-phenyl octanoic acid:

N-(N-AcetylTyrosinyl-Valinyl-Alaninyl)-3-amino-4-oxo-8-phenyl octanoic acid t-butyl ester (100 mg) was dissolved in a 1:1 mixture of $CH_2Cl_2$/TFA (10 mL). The mixture was stirred at rt for 30 min and the solvent was reduced in vacuo. The residue was recrystilized from acetone/hexane to provide the acid (80 mg, 80%)

$^1$H NMR ($CD_3OD$), δ7.23 (m, 2H), 7.15 (m, 3H), 7.03 (d, 2H), 6.68 (d, 2H) 4.58 (m, 2H), 4.32 (q, 1H), 4.13 (m, 1H), 3.0 (dd, 1H), 2.9–2.42 (m, 7H), 2.05 (m, 1H), 1.92 (s, 3H), 1.58 (m, 4H), 1.35 (d, 3H), 0.92 (m, 6H).

EXAMPLE 12

N-(N-AcetylTyrosinyl-Valinyl-Alaninyl)-3-amino-4-oxo-9-phenyl nonanoic acid:

Step A

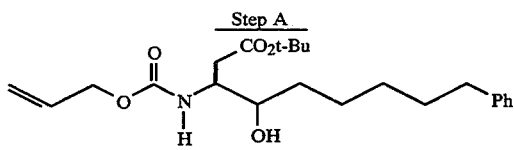

3-Allyloxycarbonylamino-4-hydroxy-9-phenyl-nonanoic acid t-butyl ester:

2M Oxallylchloride (0.82 mL) in $CH_2Cl_2$ was added to a mixture of DMSO (0.125 mL)) in $CH_2Cl_2$ (2 mL) at −78° C. The resulting mixture was stirred at −78° C. for 10 min and the N-alloc-b-t-butyl aspartic alcohol (390 mg, 1.5 mmol) in $CH_2Cl_2$ (3 mL) was added dropwise. The mixture was stirred at −78° C. for 30 min and 5 min at −20° C. The mixture was cooled to −78° C. and i-Pr$_2$NEt (0.783 mL) was added dropwise. The resulting mixture was stirred at −78° C. for 20 min and at 0° C. for 30 min. The mixture was cooled to −78° C. and (5.0 mL) 1M phenylpentyl magnesium bromide in $Et_2O$ was added dropwise. The mixture was stirred at −78° C. for 30 min and at 0° C. for 1 h. $Et_2O$ (30 mL) was added and the two layers were separated. The aqueous layer was further extracted with $Et_2O$ (3×20 mL) and the combined organic extracts were dried over $Na_2SO_4$. The solvent was reduced in vacuo. The residue was chromatographed over silica (1:1, $Et_2O$:Hexane) to provide the alcohol (460 mg, 77%).

$^1$H NMR ($CDCl_3$), δ7.25 (m, 2H), 7.15 (m, 3H), 5.91 (m, 1H), 5.3 (m, 2H), 5.18 (d, 1H), 4.55 (d, 2H), 3.9 (m, 1H), 3.65 (m, 2H), 2.55 (m, 6H), 1.6 (m, 4H), 1.45 (s, 9H), 1.35 (m, 2H).

Step B

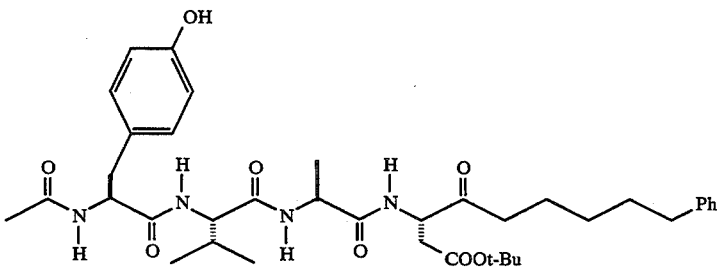

N-(N-AcetylTyrosinyl-Valinyl-Alaninyl)-3-amino-4-oxo-9-phenyl nonanoic acid t-butyl ester:

3-Allyloxycarbonylamino-4-hydroxy-9-phenyl-nonanoic acid t-butyl ester (360 mg, 0.9.5 mmol) was dissolved in $CH_2Cl_2$ (5 mL) and Dess-Martin reagent (576 mg, 1.35 mmol) was added. The resulting mixture was stirred for 2 h at rt and the mixture was filtered through a block of silica (2:1, l Hexane:$Et_2O$) to provide the phenylpentyl ketone (350 mg, 97%).

t-Butyl(3-N-alloc, 4-oxo-9-phenyl) nonanoate (260 mg, 0.653 mmol) was dissolved in $CH_2Cl_2$ (6 mL). $PdCl_2$ ($Ph_3P$)$_2$ (cat.) and $Bu_3SnH$ (0.27 mL) was added dropwise. The mixture was stirred for under $N_2$ for 10 min. DMF (12 mL), AcTyr-Val-Ala (630 mg), HOBT (132.7 mg) and EDC (155 mg) were added respectively. The resulting mixture was stirred overnight. EtOAc (150 mL) was added and the mixture was washed with aq. $NaHCO_3$ (15 mL). The solvent was reduced in vacuo and the residue was chromatographed over silica (95:5, $CH_2Cl_2$:MeOH) to afford the tetra-peptide (355 mg).

$^1$H NMR ($CD_3OD$), δ7.25 (m, 2H), 7.15 (m, 3H), 7.05 (d, 2H), 6.68 (d. 2H), 4.6 (m, 2H), 4.34 (m, 1H), 4.15 (d, 1H), 3.2 (dd, 1H), 2.65 (m, 1H), 2.55 (m, 6H), 2.05 (m, 1H), 1.91 (s, 3H), 1.58 (m, 4H), 1.42 (s, 9H), 1.35 (d, 3H), 1,3 (m, 2H), 0.90 (t, 6H).

Step C

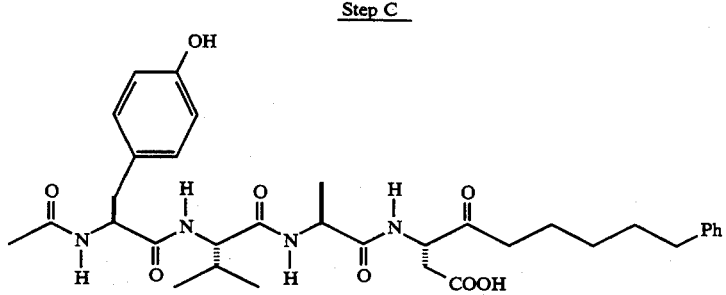

N-(N-AcetylTyrosinyl-Valinyl-Alaninyl)-3-amino-4-oxo-9-phenyl nonanoic acid:

N-(N-AcetylTyrosinyl-Valinyl-Alaninyl)-3-amino-4-oxo-9-phenyl nonanoic acid t-butyl ester (140 mg) was dissolved in a 1:1 mixture of $CH_2Cl_2$/TFA (8 mL). The mixture was stirred at rt for 30 min and the solvent was reduced in vacuo. The residue was recrystilized from acetone/hexane to provide the acid (120 mg, 80%).

$^1$H NMR ($CD_3OD$), δ7.25 (m, 2H), 7.15 (m, 3H), 7.05 (d, 2H), 6.69 (d, 2H) 4.6 (t, 2H), 4,32 (q, 1H), 4.15 (m, 1H), 3.2 (dd, 1H), 2.9–2.42 (m, 7H), 2.07 (m, 1H), 1.92 (s, 3H), 1.6 (m, 4H), 1.45 (d, 2H), 1.32 (m, 2H), 0.95 (m, 6H).

M/z $(M+K)^+$ 678.5, $(M+Na)^+$ 662.3, M+1 639.5, 622.6, 464.3, 511.2, 434.2, 377.1, 336.3, 306.1, 265, 206.8, 178.6, 136.9.

EXAMPLE 13

N-(N-AcetylTyrosinyl-Valinyl-Alaninyl)-3-amino-5-hydroxy-4-oxo-7-phenyl heptanoic acid:

Step A

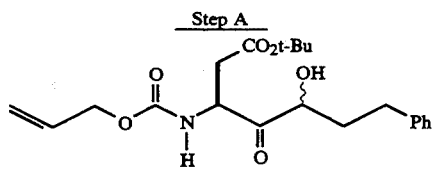

3-Allyloxycarbonylamino-5-hydroxy-4-oxo-7-phenylheptanoic acid t-butyl ester:

The 3-Allyloxycarbonylamino-4-oxo-7-phenylheptanoic acid t-butyl ester (1.112 g) was dissolved in THF (20 mL) and was cooled to −78° C. 1M LHMDS was added dropwise and the resulting mixture was stirred at for 2 h. 2-(phenylsulfonyl)-3-phenyloxaziridine (1.176 g) in THF (10 L) was added dropwise and the resulting mixture was stirred at −78° C. for 8 h. aq. $NH_4Cl$ (20 ml) was added and the two layers were separated. The aqueous layer was further extracted with EtOAc (3×20 mL). The combined organic extracts were dried over $Na_2SO_4$ and the solvent was reduced in vacuo. The residue was chromatographed over silica (1:1,Ether/Hexane) to provide the title compound (650 mg, 59%).

$^1$H NMR ($CDCl_3$), δ7.25 (m, 2H), 7.15 (m, 3H), 5.88 (m, 1H), 5.75 (t, NH), 5.25 (m, 2H), 4.68 (m, 1H), 4.55 (m, 2H), 4.42 (m, 1H), 3.25 (br., OH), 2.92 (dd, 1H), 2.8–2.45 (m, 4H). 2.12 (m, 1H), 1.8 (m, 1H), 1.38 (d, 9H).

Step B

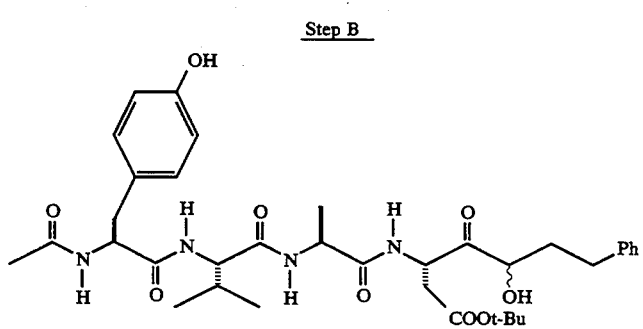

N-(N-AcetylTyrosinyl-Valinyl-Alaninyl)-3-amino-5-hydroxy-4-ozo-7-phenyl heptanoic acid t-butyl ester:

3-Allyloxycarbonylamino-5-hydroxy-4-oxo-7-phenylheptanoic acid t-butyl ester (62 mg, 0.64 mmol) was dissolved in $CH_2Cl_2$ (3 mL). $PdCl_2$ $(Ph_3P)_2$ (cat.) and $Bu_3SnH$ (0.067 mL) was added dropwise. The mixture was stirred under $N_2$ for 10 min. DMF (8 mL), AcTyr-Val-Ala (158 mg), HOBT (33 mg) and EDC (39 mg) were added respectively. The resulting mixture was stirred overnight. EtOAc (100 mL) was added and the mixture was washed with aq. $NaHCO_3$ (10 mL). The solvent was reduced in vacuo and the residue was chromatographed over silica (95:5, $CH_2Cl_2$:MeOH) to afford the tetra-peptide which was dissolved in a 1:1 to provide the title compound (98 mg).

$^1$H NMR ($CD_3OD$), δ7.3–7.1 (m, 5H), 7.05 (d, 2H), 6.68 (d. 2H), 4.58 (m, 1H), 4.35–4.2 (m, 3H), 4.15 (d, 1H), 3.0 (dd, 1H), 2.9–2.45 (m, 5H), 2.05 (m, 1H), 1.88 (s, 3H), 1.82 (m, 2H), 1.42 (s, 9H), 1.35 (dd, 3H), 0.95 (m, 6H).

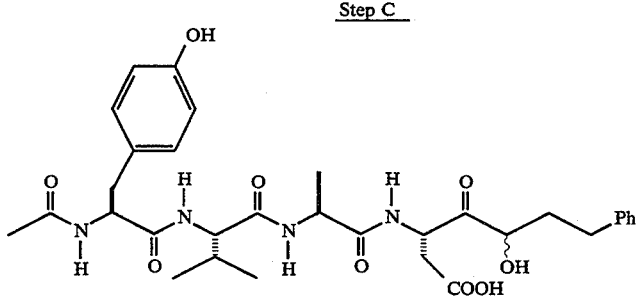

N-(N-AcetylTyrosinyl-Valinyl-Alaninyl)-3-amino-5-hydroxy-4-oxo-7-phenyl heptanoic acid:

N-(N-AcetylTyrosinyl-Valinyl-Alaninyl)-3-amino-5-hydroxy-4-oxo-7-phenyl heptanoic acid t-butyl ester (40 mg) was dissolved in a 1:1 mixture of $CH_2Cl_2$/TFA (6 mL). The mixture was stirred at room temperature for 30 min and the solvent was reduced in vacuo. The residue was recrystilized from acetone/hexane to provide the acid (33 mg).

$^1$H NMR ($CD_3OD$), δ7.3–7.1 (m, 5H), 7.07 (d, 2H), 6.9 (d. 2H), 4.55 (m, 1H), 4.35–4.25 (m, 3H), 4.17 (d, 1H), 3.03 (dd, 1H), 2.92–2.5 (m, 5H), 2.03 (m, 1H), 1.88 (s, 3H), 1.82 (m, 2H), 1.37 (dd, 3H), 0.93 (m, 6H).

m/z $(M+K)^+$ 651, $(M+Na)^+$ 635, $(M+1)$ 614, 595, 550, 522, 445, 387, 376, 305, 291, 238, 178, 119.

EXAMPLE 14

N-(3-Phenylpropionyl-Valinyl-Alaninyl) 3-amino-4-oxo-5,5-difluoro-8-phenyl Octanoic acid:

STEP A

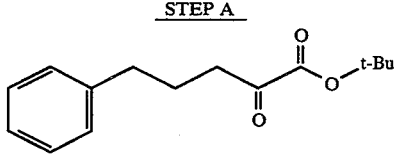

t-Buty(5-phenyl-2,2-oxo)pentanoate:

phenylpropyl bromide (7.64 mL, 50.23 mmol) was added to a suspension of magnesium turning (1.22 g, 50.23 mmol) in ether (20 mL) maintaining gentle reflux. The resulting mixture was stirred for additional 1 h and was added slowly over 30 min. to di-t-butyloxalate (10.16 g, 50.23 mmol) dissolved in $CH_2Cl_2$ (200 mL) at −78° C. The resulting mixture was stirred for 1 h and was poured into a mixture of icewater (300 mL) and 1N aq $NH_4Cl$ (300 mL) containing ether (200 mL). The two layers were separated and the aqueous layer was further extracted with ether (3×100 mL). The combined organic extracts was washed with water (2×100 mL), brine (100 mL) and dried over $Na_2SO_4$. The solvent was evaporated to provide the title compound (15.7 g).

STEP B

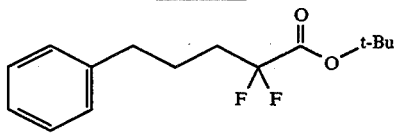

t-Butyl(5-phenyl-2,2-difluoro)pentanoate:

t-Butyl-5-phenyl-2-oxo-pentanoate (9 g) was dissolved in $CH_2Cl_2$ (140 mL) and dimethylaminofulfur triflouride (8.45 mL) was added dropwise at 0° C. The resulting mixture was stirred at rt for 18 h. the reaction mixture was cooled to 0° C. and quinched with 1N aq $NH_4Cl$. The mixture was extracted with ether (3×150 mL). The combined organic extracts was dried over $Na_2SO_4$. the solvent was evaporated and the residue was chromatographed over silica (95:5, Hexane:EtOAc) to provide the difluoro compound (6.5 g).

$^1$HNMR ($CDCL_3$), δ7.27 (2H, m) 7.15 (3H, m), 2.65 (3H, t), 2.0 (2H, m), 1.78 (m, 3H), 1.5 (s, 9H).

STEP C

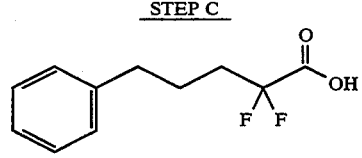

5-Phenyl-2,2-difluoro-pentanoic acid:

t-Butyl-5-phenyl-2,2-difluoro-pentanoate (0.9 g) was dissolved in a 1:1 mixture of $CH_2Cl_2$/TFA (8 mL). the mixture was stirred for 1 h. the solvent was evaporated to give the acid.

$^1$HNMR(CDCl3), d 7.29 (2H, m) 7.2 (3H, m) 2.68 (2H, t), 2.1 (2H, m), 1.85 (2H, m).

$^{19}$FNMR ($CDCL_3$), d −172.1 (2F, t, JF-H=16.7 Hz).

STEP D

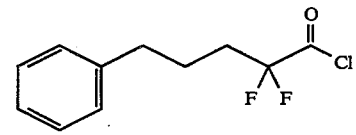

5-Phenyl-2,2-difluoro-pentanoic acid chloride:

To the 5-phenyl-2,2-difluoro-pentanoic acid (1.5 g, 7 mmol) in $CH_2Cl_2$ (3 mL) was added 2M oxalyl chloride (4.2 mL, 8.4 mmol) in $CH_2Cl_2$ and DMF (cat.). The resulting mixture was stirred at rt for 1 h. the solvent was evaporated and the residue was distilled (70°–75° C., 0.1 mmHg) to provide the acid chloride (1.25 g).

$^1$HNMR(CDCl3), δ7.29 (2H, m), 7.2 (3H, m), 2.68 (2H, t), 2.1 (2H, m), 1.85 (2H, m).

$^{19}$FNMR(CDCl3), δ− 102.2 (2F, t, JF-H=16.7 Hz).

STEP E

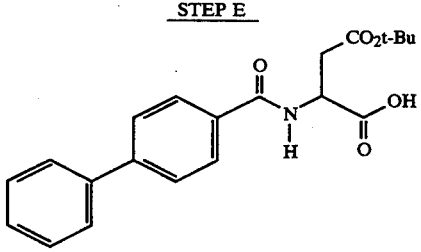

N-(4-Bi-phenylcarbonyl) b-t-butyl-Aspartic acid:

to aspartic acid (6.)g) in dry THF (100 mL) was added 4-bi-phenylcarbonyl chloride (3.44 g). the resulting mixture was stirred for 17 h. water (300 1LO) was added and the mixture was extracted with EtOAc (3×100 mL). The combined organic extracts was dried over Na2SO4 and the solvent was evaporated to provide the title compound (3.8 g).

$^1$HNMR(CDCl$_3$), δ7.88 (2H, d) 7.65 (2H, d), 7.6 (2H, d), 7.45 (2H, d), 7.38 (1H, m), 5.05 (1H, m), 3.1 (2H, dd), 2.85 (1H, dd), 1.35 (9H, s).

STEP F

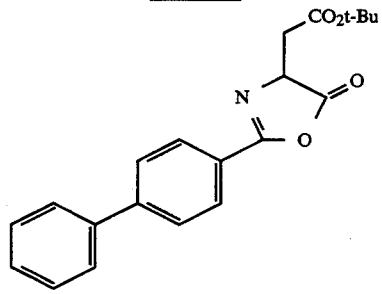

2-Bi-phenyl5(4H)-oxazolones:

To the aminoacid (5.92 g) in CH2C12 (100 ml) at 0° C. was added EDC (2.5 g). The resulting mixture was stirred for 30 min, Ether (300 ml) was added and the mixture was washed with water (50 mL). The mixture was dried with Na2SO4 and the solvent was evaporated. The residue was chromatographed over silica (1:1,ether:hexane) to afford the oxazolone compound (4.6 g).

$^1$HNMR(CDCl$_3$) δ8.05 (2H, d), 7.7 (2H, d), 7.62 (2H, d), 7.45 (2H, d), 7.39 (1H, m), 4.54 (1H, t), 3.03 (2H, ABq), 1.35 (9H, s).

STEP G

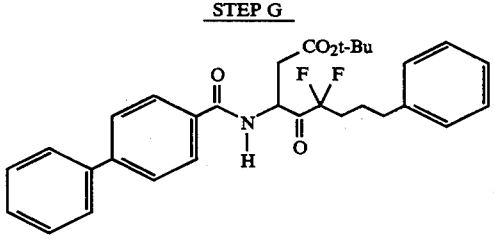

3-(4-Bi-phenylcarbonylamino)-4-oxo-5,5-difluoro-8-phenyoctanoic acid t-butylester:

To 5(4H)-oxazolones in dry THF (3 mL) at 0° C. under nitrogen atmosphere was added Et3N (0.167 mL) and freshly prepared solution of 5-phenyl-2,2-difluoropentanoic acid chloride (280 mg) in dry hexane (1 mL). The reaction mixture was stirred for 1 h at room temperature. The mixture was filtered under N$_2$ atmosphere and the filtrate evaporated thoroughly (0.005 torr, 17 h). The crude O-acylated oxazoles was then diluted with dry THF (0.2 mL) and 4-dimethylaminopyridine (12.25 mg) is added. The mixture was stirred for 2 h and the solvent was removed. The residue was treated with oxalic acid (180 mg) and the resulting mixture was stirred for 18 h. EtOAc (150 mL) was added and the mixture was washed with aq. NaHCO$_3$ (2×20 mL), water (2×20 mL), Brine (20 mL) and dried over Na$_2$SO$_4$. The solvent was removed and the residue was chromatographed over silica (99:1 CH$_2$Cl$_2$:EtOH) to provide the title compound (170 mg)

$^1$HNMR(CDCl$_3$) d 7.85 (2H, d), 7.67 (2H, d), 7.6 (2H, d), 7.45 (2H, t), 7.35 (2H, m), 7.26 (2H, d), 7.17 (2H, t), 5.35 (1H, m), 3.05 (1H, dd), 2.95 (1H, dd), 2.68 (2H, d), 2.13 (2H, m), 1.85 (1H, m), 1.42 (9H, s).

$^{19}$FNMR(CDCl$_3$), d −103.6 and −104.45 (1F, t, J$_{F-H}$=17.4 Hz, J$_{F-F}$=278.1 Hz), −107.03 and −107.83 (1F, t, J$_{F-H}$=18.4 Hz, J$_{F-F}$=278.4 Hz).

STEP H

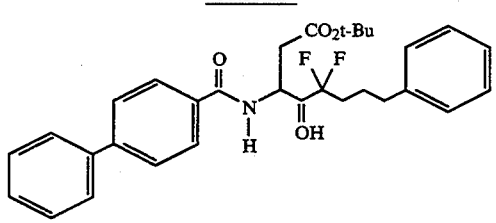

3-(4-Bi-phenylcarbonylamino)-4-hydroxy-5,5-difluoro-8-phenyloctanoic acid t-butylester:

To 3-(4-Bi-phenylcarbonylamino)-4-oxo-5,5-difluoro-8-phenyl octanoic acid t-butylester (330 mg) in MeOH (2 mL) at 0° C. was added NaBH4 (20 mg). The mixture was warmed to rt and stirred for 5 min. 1N NH4Cl (3 mL) was added and the mixture was extracted with EtOAc (3×10 mL). The combined extracts was dried over Na2SO4 and the solvent was evaporated. The residue was chromatographed over silica (1:1, EtOAc:hexane) to provide the title compound (270 mg)

STEP I

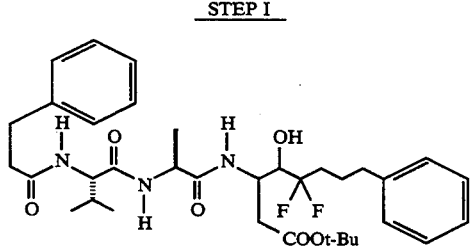

N-(3-Phenylpropionyl-Valinyl-Alaninyl) 3-amino-4-hydroxy-5,5-difluoro-8-phenyl t-butyloctanoate:

To 3-(4-Bi-phenylcarbonylamino)-4-hydroxy-5,5-difluoro-8-phenyloctanoic acid t-butylester (252 mg, 0.5 mmol) in MeOH (5 mL) was added 3% Na-Hg (4 mmol, 8 eq) and NaHh$_2$PO$_4$ (6 mmol, 12 eq). The mixture was stirred at rt for 1 h and filtered into 1N aq HCl (8 eq). MeOH was removed and the solid was filtered and washed with water. The residue was lyophilized to give a white solid. (100 mg, 0.29 mmol) which was dissolved in DMF (3 mL) followed by addition of HOBT (43.3 mg), EDC (61 mg) and N-phenylpropionyl Val Ala (110 mg). The resulting mixture was stirred for 17 h and EtOAc (100 ml) was added. The mixture was washed with aq NaHCO₃, water and dried over Na₂SO₄. The solvent was evaporated and the residue was chromatographed over silica (95:5, CH₂Cl₂:MeOH) to provide the title compound (150 mg)

STEP J

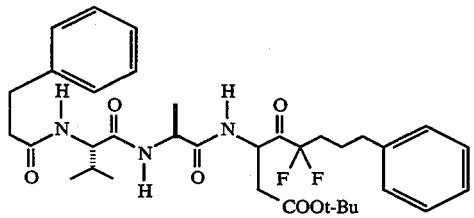

N-(3-Phenylpropionyl-Valinyl-Alaninyl) 3-amino-4-oxo-5,5-difluoro-8-phenyl t-butyloctanoate:

To N-(3-Phenylpropionyl-Valinyl-Alaninyl) 3-amino-4-hydroxy-5,5-difluoro-7-phenyl t-butylheptanoate (150 mg) in CH₂Cl₂ (5 mL) was added Dess-Martin reagent (750 mg). The mixture was stirred for 5 h and filtered. The solvent was evaporated and the residue was chromatographed over silica (95:5, CH₂Cl₂:MeOH) to provide the title compound (130 mg)

STEP K

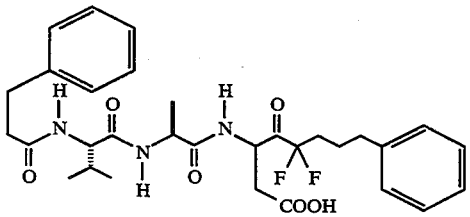

N-(3-Phenylpropionyl-Valinyl-Alaninyl) 3-amino-4-oxo-5,5-difluoro-8-phenyl Octanoic acid N-(3-Phenylpropionyl-Valinyl-Alaninyl) 3-amino-4-oxo-5,5-difluoro-7-phenyl t-butylheptanoate (130 mg) was dissolved in a 1:1 mixture of CH₂Cl₂/TFAA (6 ml) and stirred for 1 h. The solvent was evaporated to provide the title compound (110 mg).

What is claimed is:

1. A compound of formula I

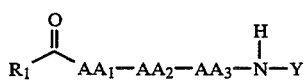

wherein Y is:

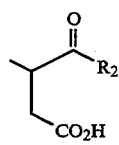

$R_1$ is $C_{1-3}$alkyl or aryl $C_{1-6}$ alkyl wherein aryl is phenyl or naphthyl;

$R_2$ is hydrogen, $AA_1$ is selected from the group consisting of
 (a) a single bond, and
 (b) an amino acid of formula AI

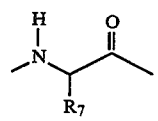

wherein $R_7$ is $C_{1-6}$ alkyl or aryl $C_{1-6}$ alkyl
 wherein aryl is defined as
  (1) phenyl, or
  (2) naphthyl,
and wherein aryl is optionally mono or di-substituted, the substituents being each independently $C_{1-6}$alkyl, halo, hydroxy, $C_{1-6}$alkyl amino, $C_{1-6}$alkoxy, $C_{1-6}$alkylthio, or $C_{1-6}$alkylcarbonyl;

$AA_2$ is an amino acid of formula AII

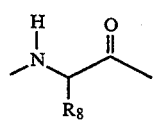

$AA_3$ is an amino acid of formula AIII

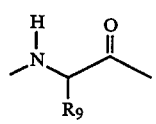

$R_8$ and $R_9$ are each individually
 (a) hydrogen,
 $C_{1-6}$alkyl, or
 (j) amino-$C_{1-6}$alkyl or N-substituted amino-$C_{1-6}$alkyl wherein the substituent is carbobenzoxy.

2. A compound According to claim 1 wherein:
$R_1$ is methyl or phenyl $C_{1-6}$ alkyl or hydroxy-phenyl $C_{1-6}$ alkyl;
$AA_1$ is a single bond or an amino acid of formula AI

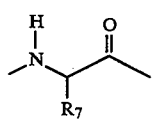

wherein $R_7$ is
 (a) $C_{1-6}$alkyl;
 (b) substituted phenyl $C_{1-3}$alkyl, wherein the substituent is hydrogen, hydroxy, carboxy, or $C_{1-4}$alkyl;
$R_8$ is $C_{1-6}$alkyl; and
$R_9$ is
 (a) hydrogen,
 (b) $C_{1-6}$alkyl,
 (c) amino $C_{1-4}$alkyl,
 (d) N-carbobenzoxy-amino-(n-butyl).

3. A compound according to claim 2
wherein $R_7$ is
 (a) $C_{1-6}$alkyl; or
 (b) substituted phenyl $C_{1-3}$alkyl, wherein the substituent is hydrogen or hydroxy.

4. A compound according to claim 3 where
$R_1$ is methyl or phenyl $C_{1-6}$ alkyl or hydroxy-phenyl $C_{1-6}$ alkyl;

AA₁ is a single bond or tyrosinyl, homotyrosinyl, phenylalaninyl, homophenylalaninyl or tryptophanyl;

AA₂ is

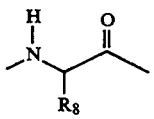

wherein R₈ is C₁₋₄ alkyl; and
AA₃ is alaninyl, lysinyl or ε-CBZ-lysinyl.

5. A compound according to claim 4 wherein
R₁ is phenyl C₁₋₆ alkyl or hydroxy-phenyl C₁₋₆ alkyl;
R₂, R₁₀ and R₁₁ are individually hydrogen;
AA1 is a single bond,;
AA2 is

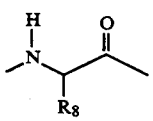

wherein R₈ is C₁₋₄ alkyl; and
AA3 is alaninyl, lysinyl or ε-CBZ-lysinyl.

6. A compound according to claim 5 wherein
R₁ is phenyl ethyl or hydroxy-phenyl ethyl.

7. A compound according to claim to claim 4 wherein
R₁ is methyl;
AA₁ is tyrosinyl, homotyrosinyl, phenylalaninyl, homophenylalaninyl or tryptophanyl;
AA2 is

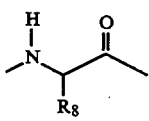

wherein R₈ is C₁₋₄ alkyl; and
AA₃ is alaninyl, lysinyl or ε-CBZ-lysinyl.

8. A compound according to claim 7 wherein
R₁ is methyl;
AA₁ is tyrosinyl;
AA₂ is valinyl, leucinyl or isoleucinyl; and
AA₃ is alaninyl, lysinyl or ε-CBZ-lysinyl.

9. A compound according to claim 8 wherein
R₁ is methyl;
AA₁ is tyrosinyl;
AA₂ is valinyl;
AA₃ is alaninyl, lysinyl or ε-CBZ-lysinyl.

10. A compound selected from the group consisting of:
(a) N-(N-Acetyl-tyrosinyl-valinyl-lysinyl)-3-amino-4-oxobutanoic acid;
(b) N-(N-Acetyl-tyrosinyl-valinyl-ε-CBZ-lysinyl)-3-amino-4-oxobutanoic acid; and
(c) N-(N-Acetyl-tyrosinyl-valinyl-alaninyl)-3-amino-4-oxobutanoic acid;
or a ring chain tautomer or hydrate thereof.

11. A compound selected from the group consisting of:
(a) N-(N-Acetyl-phenylalaninyl-valinyl-lysinyl)-3-amino-4-oxobutanoic acid;
(b) N-(N-Acetyl-phenylalaninyl-valinyl-ε-CBZ-lysinyl)-3-amino-4-oxobutanoic acid; and
(c) N-(N-Acetyl-phenylalaninyl-valinyl-alaninyl)-3-amino-4-oxobutanoic acid;
(d) N-(3-phenylpropionyl-valinyl-lysinyl)-3-amino-4-oxobutanoic acid;
(e) N-(3-phenylpropionyl-valinyl-ε-CBZ-lysinyl)-3-amino-4-oxobutanoic acid;
(f) N-(3-phenylpropionyl-valinyl-alaninyl)-3-amino-4-oxobutanoic acid;
(g) N-(3-(4-hydroxyphenyl)-propionyl-valinyl-lysinyl)-3-amino-4-oxobutanoic acid;
(h) N-(3-(4-hydroxyphenyl)-propionyl-valinyl-ε-CBZ-lysinyl)-3-amino-4-oxobutanoic acid; and
(i) N-(3-(4-hydroxyphenyl)-valinyl-alaninyl)-3-amino-4-oxobutanoic acid;
(n) N-(N-acetyl-tyrosinyl-valinyl-(N,N)-dimethyl-Lisinyl)-3-amino-4-oxo-butanoic acid;
(o) N-(N-phenylpropionyl)valinyl-glycinyl)-3-amino-4-oxo-butanoic acid;
(p) N(N-acetyl-alaninyl)-3-amino-4-oxo-butanoic acid;
(q) N-(N-acetyl-valinyl-alaninyl)-3-amino-4-oxo-butanoic acid;
(r) N-propionyl-3-amino-4-oxo-butanoic acid;
(s) N-(N-acetyl-3-amino-4-oxo-butanoic acid; or
(t) N-(N-Acetyl tyrosinyl-valinyl-histidinyl-3-amino-4-oxo butanac acid.

12. A compound which is
N-(N-Acetyl-tyrosinyl-valinyl-alaninyl)-3-amino-4-oxobutanoic acid.

13. A compound of formula I

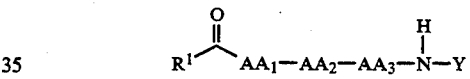

wherein Y is:

R₁ is C₁₋₃alkyl or aryl C₁₋₆ alkyl wherein aryl is phenyl, naphthyl, thienyl, or benzothienyl;
R₂ is

R₄
—C—R₆,
R₅ wherein R₄ and R₅ are each individually hydrogen;
R₆ is
   aryl C₁₋₆ alkyl,
wherein the alkyl is substituted with hydrogen, oxo, C₁₋₃ alkyl, halo or hydroxy wherein aryl is selected from the group consisting of
   (1) phenyl,
   (2) naphthyl,
   (3) pyridyl, and
wherein the aryl is optionally mono or di-substituted, the substituents being each independently C₁₋₃alkyl, halo, hydroxy, C₁₋₃alkyl amino, C₁₋₃alkoxy, C₁₋₃alkylthio, or C₁₋₃alkylcarbonyl;
AA₁ is selected from the group consisting of
   (a) a single bond, and
   (b) an amino acid of formula AI

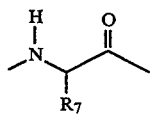

$R_7$ is $C_{1-6}$alkyl or aryl $C_{1-6}$ alkyl
wherein aryl is defined as above in this claim, and wherein the aryl is optionally mono or di-substituted, the substituents being each independently $C_{1-6}$alkyl, halo, hydroxy, $C_{1-6}$alkyl amino, $C_{1-6}$alkoxy, $C_{1-6}$alkylthio, or $C_{1-6}$alkylcarbonyl, $AA_2$ is an amino acid of formula AII

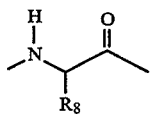

$AA_3$ is an amino acid of formula AIII $R_8$ and $R_9$ are each individually
   (a) hydrogen,
   (b) $C_{1-6}$alkyl
   (j) amino-$C_{1-6}$alkyl or N-substituted amino-$C_{1-6}$alkyl wherein the substituent is carbobenzoxy, or.

14. A compound according to claim 13 wherein
$R_6$ is
   phenyl $C_{1-6}$ alkyl,
wherein the alkyl is substituted with hydrogen, oxo, $C_{1-3}$ alkyl, halo or hydroxy, and wherein the phenyl may be mono and di-substituted, the substituents being each independently $C_{1-3}$alkyl, halo, hydroxy, $C_{1-3}$alkyl amino, $C_{1-3}$alkoxy, $C_{1-3}$alkylthio, or $C_{1-3}$alkylcarbonyl;
$R_9$ is
   (a) hydrogen,
   (b) $C_{1-6}$alkyl,
   (c) amino $C_{1-4}$alkyl, or
   (d) N-carbobenzoxy-amino-(n-butyl).

15. A compound according to claim 14 wherein $R_7$ is
   (a) $C_{1-6}$alkyl; or
   (b) substituted phenyl $C_{1-3}$alkyl, wherein the substituent is hydrogen or hydroxy.

16. A compound according to claim 15 wherein $R_6$ is
   (a) phenyl methyl,
   (b) phenyl ethyl,
   (c) phenyl propyl,
   (d) phenyl butyl, or
   (e) phenyl pentyl;
$R_1$ is methyl or phenyl $C_{1-6}$ alkyl or hydroxy-phenyl $C_{1-6}$ alkyl;
$AA_1$ is a single bond or tyrosinyl, homotyrosinyl, phenylalaninyl, homophenylalaninyl or tryptophanyl;
$AA_2$ is

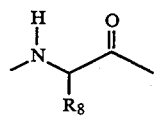

wherein R8 is $C_{1-4}$ alkyl; and
   $AA_3$ is alaninyl, lysinyl or ε-CBZ-lysinyl.

17. A compound according to claim 16 wherein
$R_1$ is phenyl $C_{1-6}$ alkyl or hydroxy-phenyl $C_{1-6}$ alkyl;
$AA_1$ is a single bond;
$AA_2$ is

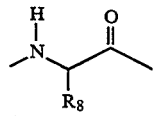

wherein R8 is $C_{1-4}$ alkyl; and
   AA3 is alaninyl, lysinyl or ε-CBZ-lysinyl.

18. A compound according to claim 17 wherein
$R_1$ is methyl, phenyl ethyl or hydroxy-phenyl ethyl.

19. A compound according to claim 18 wherein
$R_1$ is methyl;
$AA_1$ is tyrosinyl, homotyrosinyl, phenylalaninyl, homophenylalaninyl or tryptophanyl;
$AA_2$ is

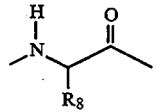

wherein $R_8$ is $C_{1-4}$ alkyl; and
   $AA_3$ is alaninyl, lysinyl or ε-CBZ-lysinyl.

20. A compound according to claim 19 wherein
$R_1$ is methyl;
$AA_1$ is tyrosinyl;
$AA_2$ is valinyl, leucinyl or isoleucinyl; and
$AA_3$ is alaninyl, lysinyl or ε-CBZ-lysinyl.

21. A compound according to claim 20 wherein
$R_1$ is methyl;
$AA_1$ is tyrosinyl;
$AA_2$ is valinyl;
$AA_3$ is alaninyl, lysinyl or ε-CBZ-lysinyl.

22. A compound selected from the group consisting of:
   (a) N-(3-Phenylpropionyl-Valinyl-Alaninyl)3-amino-4-oxo-5-phenylpentanoic acid;
   (b) N-(3-Phenylpropionyl-Valinyl-Alaninyl)3-amino-4-oxo-6-phenylhexanoic acid;
   (c) N-(3-Phenylpropionyl-Valinyl-Alaninyl)3-amino-4-oxo-7-phenylheptanoic acid;
   (d) N-(N-AcetylTyrosinyl-Valinyl-Alaninyl)-3-amino-4-oxo-7-phenyl heptanoic acid;
   (e) N-(N-AcetylTyrosinyl-Valinyl-Alaninyl)-3-amino-4-oxo-8-phenyl octanoic acid;
   (f) N-(N-AcetylTyrosinyl-Valinyl-Alaninyl)-3-amino-4-oxo-9-phenyl nonanoic acid; or
   (g) N-(N-AcetylTyrosinyl-Valinyl-Alaninyl)-3-amino-5-hydroxy-4-oxo-7-phenyl heptanoic acid.

* * * * *